(12) United States Patent
Miyanohara

(10) Patent No.: US 8,045,012 B2
(45) Date of Patent: Oct. 25, 2011

(54) IMAGE-PICKUP APPARATUS

(75) Inventor: Makoto Miyanohara, Tokyo (JP)

(73) Assignee: Olympus Corporation, Tokyo (JP)

( * ) Notice: Subject to any disclaimer, the term of this patent is extended or adjusted under 35 U.S.C. 154(b) by 772 days.

(21) Appl. No.: 11/677,788

(22) Filed: Feb. 22, 2007

(65) Prior Publication Data

US 2007/0216781 A1 Sep. 20, 2007

(30) Foreign Application Priority Data

Feb. 24, 2006 (JP) .................................. 2006-047951

(51) Int. Cl.
*H04N 5/225* (2006.01)
*H04N 5/76* (2006.01)
*A61B 1/04* (2006.01)
*A61M 37/00* (2006.01)

(52) U.S. Cl. ............... 348/218.1; 348/231.99; 600/109; 600/12; 600/309

(58) Field of Classification Search ............... 348/218.1, 348/231.99; 600/309
See application file for complete search history.

(56) References Cited

U.S. PATENT DOCUMENTS

| 5,877,819 | A  | * | 3/1999  | Branson ........................... 348/701 |
| 6,337,928 | B1 | * | 1/2002  | Takahashi et al. ............. 382/236 |
| 2001/0021223 | A1 | * | 9/2001  | Andrew .................... 375/240.11 |
| 2001/0051766 | A1 | * | 12/2001 | Gazdzinski ................... 600/309 |
| 2003/0133024 | A1 | * | 7/2003  | Ohnishi .................... 348/231.99 |
| 2004/0061778 | A1 | * | 4/2004  | Yamane et al. ................. 348/86 |
| 2004/0258308 | A1 | * | 12/2004 | Sadovsky et al. ............. 382/190 |
| 2005/0036659 | A1 | * | 2/2005  | Talmon et al. ................. 382/103 |
| 2006/0093224 | A1 | * | 5/2006  | Uchino ......................... 382/232 |
| 2006/0103731 | A1 | * | 5/2006  | Pilu et al. ................. 348/207.99 |
| 2006/0109339 | A1 | * | 5/2006  | Chao et al. ................. 348/14.01 |

FOREIGN PATENT DOCUMENTS

| JP | 6-213730 A | 8/1994 |
| JP | 10-66074 A | 3/1998 |
| JP | 2000-059758 A | 2/2000 |
| JP | 2000-184367 A | 6/2000 |
| JP | 2002-171434 A | 6/2002 |
| JP | 2002-171484 A | 6/2002 |
| JP | 2002-320084 A | 10/2002 |
| JP | 2004-120624 A | 4/2004 |
| JP | 2005-323046 A | 11/2005 |
| WO | 2004/054430 A2 | 7/2004 |

OTHER PUBLICATIONS

Japanese Office Action dated Nov. 2, 2010, issued in corresponding Japanese Patent Application No. 2006-047951.
Japanese Office Action dated May 31, 2011, issued in corresponding Japanese Patent Application No. 2006-047951.

* cited by examiner

*Primary Examiner* — David Ometz
*Assistant Examiner* — Quang V Le
(74) *Attorney, Agent, or Firm* — Westerman, Hattori, Daniels & Adrian, LLP

(57) ABSTRACT

An image-pickup apparatus includes: an image-pickup device for converting light into an electric signal and outputting a first image data; a transmitting unit for successively transmitting the first image data to an apparatus in the exterior of the image-pickup apparatus; and a storage unit for storing a second image data extracted from the first image data per frame unit under a predetermined condition.

6 Claims, 26 Drawing Sheets

FIG. 3
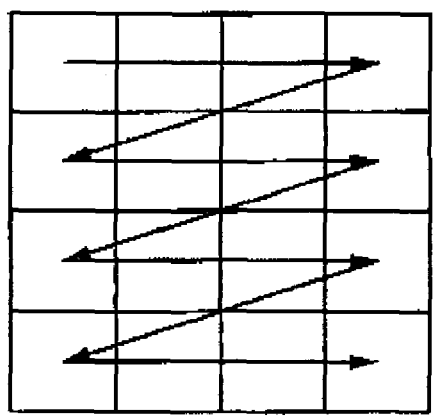
FIG. 4A
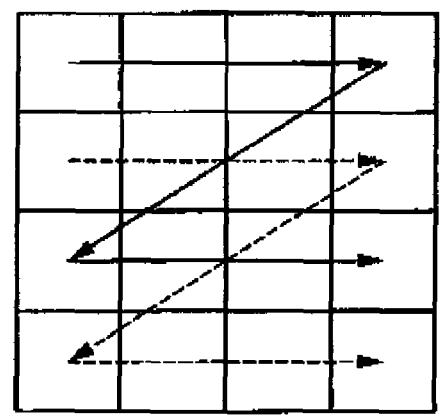
FIG. 4B
ODD FIELD ⎯⎯⎯→
EVEN FIELD -------→

FIG. 29
MAXIMUM TRANSMISSION RATE: 40 Mbit/sec.
PIXEL-SUBSAMPLING-CIRCUIT   SUBSAMPLING-CONTROLLING CIRCUIT
STILL STATE
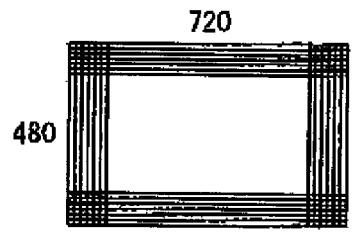
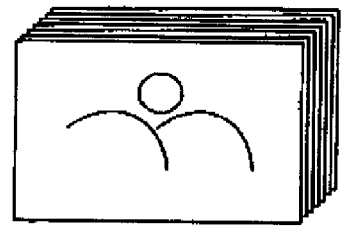
7 FRAMES/sec.
MOVING STATE
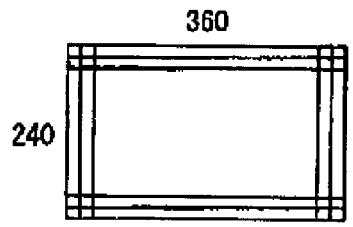
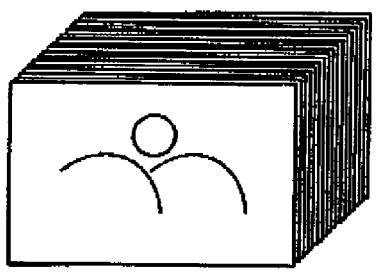
30 FRAMES/sec.

IMAGE-PICKUP APPARATUS

The present application claims priority on patent application No. 2006-047951 filed in Japan Feb. 24, 2006, the content of which is incorporated herein by reference.

BACKGROUND OF THE INVENTION

1. Field of the Invention

The preset invention relates to an image-pickup apparatus for transmitting a picked up image through a transmitting path and, in particular, to an image-pickup apparatus desirable for use in a small device having a lower transmission rate of transmitting path, e.g., an endoscope system, a surveillance camera, an on-board camera, and an image-pickup module for a videophone.

2. Description of the Related Art

In many proposed examples in response to recent requirements for a smaller image-pickup apparatus, an image-pickup-and-display system has a section for picking up an image and a section for displaying the picked up image sent through a specific transmitting path, both sections being disposed separately. An example of such an image-pickup-and-display system is illustrated in FIG. 27 in a schematic view. As shown in FIG. 27, an image-pickup apparatus 1 is constructed by an image-pickup section 3, an image-compressing section 4, and a data-transmitting section 5. Meanwhile, an image-displaying apparatus 2 is constructed by a data-receiving section 6, an image-decompressing section 7, and an image-displaying section 8.

The image-pickup section 3 receives light emitted from an object at a predetermined time interval and generates an image data corresponding to the amount of light received. The image-compressing section 4 compresses and encodes the image data based on a predetermined compressing condition and generates an encoded data. The data-transmitting section 5 transmits the encoded data to the image-displaying apparatus 2 through a transmitting path having a predetermined transfer rate. The data-receiving section 6 receives an encoded data that is transmitted from the image-pickup apparatus 1 trough a transmitting path. The image-decompressing section 7 decompresses and decodes the encoded data using a decompressing method corresponding to the compressing method used in the image-compressing section 4 and generates an image data. The image-displaying section 8 shows the image based on the image data.

One of the envisaged applications of the above image-pickup-and-display system is that the image-pickup apparatus 1 first picks up an image, the image-displaying apparatus 2 then displays the picked up image at a separate location from the image-pickup apparatus 1, and the displayed image is ready to be viewed. However, in a case where transmitting paths used in the image-pickup-and-display system shown in FIG. 27 have a somewhat low bit-rate (transfer rate), the image data picked up by the image-pickup section 3 must be sub-sampled at a predetermined time interval; or the image data must be compressed and encoded by the image-compressing section 4. Therefore, inevitably the frame rate lowers and the image exhibited by the image-displaying apparatus 2 is deteriorated.

Japanese Unexamined Patent Application, First Publication No. H10-066074 discloses an image-transmitting apparatus proposed in response to the above disadvantages. FIG. 28 is a schematic view of the image-transmitting apparatus. A shooting lens 10 shown in FIG. 28 transmits incident light therethrough and emits the light onto an image-pickup device 12. An image-pickup device 12 conducts photoelectric conversion of the emitted light. A CDS/AGC circuit 14 conducts double sampling and automatic gain control of the electric signal. An A/D converter 16 converts the analogue electric signal into a digital signal. A digital-signal-processing circuit 18 conducts data-processing of the digital signal.

A motion-detecting circuit 20 determines whether the object image in the digital image data is a moving image or a still image by detecting a motion vector. A pixel-sub-sampling-circuit 22 conducts sub-sampling of pixels in the image data based on the detection conducted with respect to the motion by the motion-detecting circuit 20. A memory 24 stores the image data temporarily. A sub-sampling-controlling circuit 26 conducts sub-sampling of pixels of the image data based on the detection conducted with respect to the motion by the motion-detecting circuit 20. A spectrum-spreading-and-transmitting circuit 28 conducts radio wave transmission of the image data from a transmitting antenna 30 using a spectrum-spreading method.

If the detection results obtained by the motion-detecting circuit 20 in the above-explained image-transmitting apparatus indicate that the object in the image data is moving, the pixel-sub-sampling-circuit 22 conducts sub-sampling of the pixels of the image data. If the detection results alternatively indicate that the object in the image data is not moving, i.e., a still image, the sub-sampling-controlling circuit 26 conducts sub-sampling of the image data.

FIG. 29 shows a concept of operations conducted by a pixel-sub-sampling-circuit 22 and the sub-sampling-controlling circuit 26. After being subject to the data-processing, the still image has 720 by 480 pixels in size obtained by the pixel-sub-sampling-circuit 22; and a frame rate of 7 fps obtained by the sub-sampling-controlling circuit 26. The moving image has 360 by 240 pixels in size and a frame rate of 30 fps. Bit rates in the two types of image data are approximately the same. The image data is switched based on the determination result with reset to (1) still image or (2) moving image obtained by the motion-detecting circuit 20, and the image transmitting apparatus transmits the selected image data.

The configuration of the image-transmitting apparatus has realized an improved quality in both the moving image and the still image that are transmitted through a transmitting path having a somewhat low bit rate because priority of the data-processing is placed on smoothness of movement in a case where the object is moving in the image; and priority of the data-processing is placed on resolution in a case of a still image.

SUMMARY OF THE INVENTION

The present invention provides an image-pickup apparatus which includes: an image-pickup device for converting light into an electric signal and outputting a first image data; a transmitting unit for successively transmitting the first image data to an apparatus in the exterior of the image-pickup apparatus; and a storage unit for storing a second image data extracted from the first image data per frame unit under a predetermined condition.

The image-pickup apparatus according to the present invention further includes a data-mount-reducing unit for reducing data amount from a corresponding frame of the corresponding first image data, and the transmitting unit transmits the first image data reduced data amount to the exterior apparatus.

The image-pickup apparatus according to the present invention further includes a frame-extracting unit for extracting the second image data per frame unit from the first image data under the predetermined condition.

The frame-extracting unit extracts the second data in accordance with an instruction supplied from the exterior apparatus in the image-pickup apparatus according to the present invention.

The image-pickup apparatus according to the present invention further includes an information-obtaining unit for obtaining characteristic information which characterized the first image data, and the frame-extracting unit extracts the second image data based on the characteristic information.

The image-pickup apparatus according to the present invention further includes an image-analyzing unit for analyzing the first image data, and the frame-extracting unit extracts the second image data based on the analysis result obtained by the image-analyzing unit.

The image-pickup apparatus according to the present invention further includes: an information-maintaining section for maintaining first characteristic information corresponding to a preceding frame of the fist image data; and an arithmetic-analyzing section for generating a signal corresponding to the varying state of the inter-frame characteristic information and outputting the analysis result, the generation of the varying-state signal being based on the first characteristic information maintained in the information-maintaining section and the second characteristic information corresponding to a succeeding frame of the first data.

In the image-pickup apparatus according to the present invention, the information-maintaining section maintains the frame corresponding to the first image data; the arithmetic-analyzing section calculates a motion vector between the frames based on the preceding frame maintained in the information-maintaining section and the succeeding frame; generates a signal corresponding to the varying state of the motion vector; and outputs the analysis result.

The image-pickup apparatus according to the present invention further includes an image-compressing section for compressing the frame associated with the first image data under a predetermined compressing condition. The information-maintaining section maintains a coded amount associated with the compressed and encoded first image data; the arithmetic-analyzing section calculates a difference in value between the coded amount of the preceding frame maintained in the information-maintaining section and the coded amount associated with the compressed and encoded succeeding frame; generates a signal corresponding to the varying state of the difference in value; and outputs the analysis result.

In the image-pickup apparatus according to the present invention, the arithmetic-analyzing section further has a threshold-value-maintaining section for maintaining a predetermined threshold; generating a signal corresponding to the varying state of the inter-frame characteristic information based on the threshold maintained by the threshold-value-maintaining section; and outputting the analysis result.

In the image-pickup apparatus according to the present invention, the frame-extracting unit extracts the preceding frame of the first image data as the second image data while the succeeding frame associated with the first image data does not extract.

The image-pickup apparatus according to the present invention further includes an image-trimming section for trimming a region corresponding to a center of the first image data extracted as the second image data.

In the image-pickup apparatus according to the present invention, the frame associated with the second image data and extracted by the frame-extracting unit is a frame succeeding the frame corresponding to the first image data associated with the analysis result.

In the image-pickup apparatus according to the present invention, the number of frames with respect to the second image data is set, and the frame-extracting unit extracts the successive frames of first image data corresponding to the number of frames set with respect to the second image data based on the setting.

The image-pickup apparatus according to the present invention further includes a data-amount-reducing unit for reducing data amount associated with the second image data, and the storage unit stores the second image data reduced data amount.

In the image-pickup apparatus according to the present invention, the data-amount-reducing unit is adaptive to set a plurality of methods for reducing the data amount.

The image-pickup apparatus according to the present invention further includes an information-obtaining unit for obtaining characteristic information which characterizes the first image data, and the data-amount-reducing unit sets a method for reducing the data amount based on the characteristic information.

The image-pickup apparatus according to the present invention further includes an information-obtaining unit for obtaining characteristic information which characterizes the first image data, and the storage unit stores the second image data to which the characteristic information is added.

In the image-pickup apparatus according to the present invention, the transmitting unit transmits the first image data to which a flag indicating that the second image data exists in the storage unit.

In the image-pickup apparatus according to the present invention, the transmitting unit transmits the second image data stored it the storage unit instead of the first image data.

In the image-pickup apparatus according to the present invention, the transmitting unit transmits the second image data stored in the storage unit instead of the first image data based on an instruction supplied by the exterior apparatus.

The image-pickup apparatus according to the present invention further includes an information-obtaining unit for obtaining characteristic information which characterized the first image data, and the transmitting unit transmits the second image data stored in the storage unit instead of the first image data based on the characteristic information.

The image-pickup apparatus according to the present invention further includes an image-analyzing unit for analyzing the first image data, wherein the transmitting unit transmits the second image data stored in the storage unit instead of the first image data based on the analysis result obtained by the image-analyzing unit.

The image-pickup apparatus according to the present invention, the transmitting unit transmits the second image data stored in the storage unit instead of the first image data based on the remaining capacity of the storage unit.

In the image-pickup apparatus according to the present invention, the information-generating section obtains at least characteristic information associated with temperature information, pH information, blood information, time information, and positional information.

The image-pickup apparatus according to the present invention further includes an output-controlling unit for controlling the output of the second image data from the storage unit to the exterior apparatus.

BRIEF DESCRIPTION OF THE DRAWINGS

FIG. 3 shows arrangement of a color filter provided to an image-pickup device in the image-pickup apparatus according to the first embodiment of the present invention.

FIGS. 4A and 4B each show an order of reading out an electric signal from an image-pickup device provided to the image-pickup apparatus according to the first embodiment of the present invention.

FIG. 29 is a schematic diagram for illustrating the operation of the conventional image-transmitting apparatus.

DETAILED DESCRIPTION OF THE INVENTION

Figure 1:
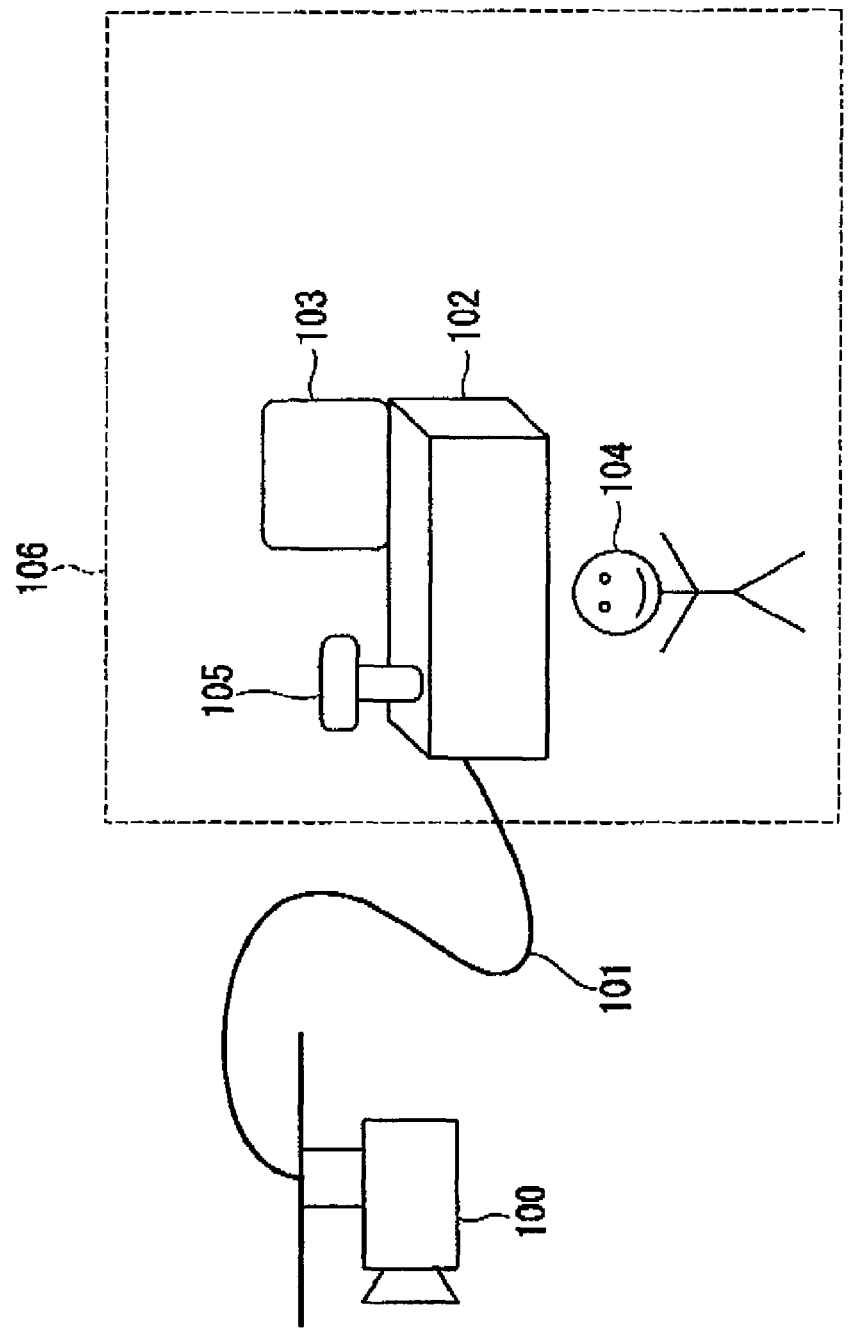
FIG. 1 is a schematic view of a surveillance camera system according to a first embodiment of the present invention.

Embodiments of the present invention will be explained below with reference to the drawings. A first embodiment of the present invention will be explained with reference to an example of an image-pickup apparatus of the present invention applied to a surveillance camera system. FIG. 1 shows a schematic view of the surveillance camera system according to the present embodiment. A surveillance camera 100 shown in FIG. 1 picks up an image of areas subject to surveillance. Data of the image picked up by the surveillance camera 100 is transmitted to a remote surveillance center 106 through a transmission cable 101. A data-processing apparatus 102 conducts predetermined data-processing on the transmitted image data in the surveillance center 106. After that, the processed image data is stored or displayed on a monitor 103.

The image displayed on the monitor 103 is supervised by a surveillant. In a case where image data are transmitted from a plurality of surveillance cameras, operations conducted by the surveillant using an operation unit 105 are, switching the images displayed on the monitor 103 and operation modes of the surveillance camera 100, etc. An electric signal indicative of the information set associated with the operation mode is transmitted to a surveillance camera 100 through a transmission cable 101. Upon receiving the electric signal, the surveillance camera 100 carries out the operations set in accordance with the operation mode.

Figure 2:
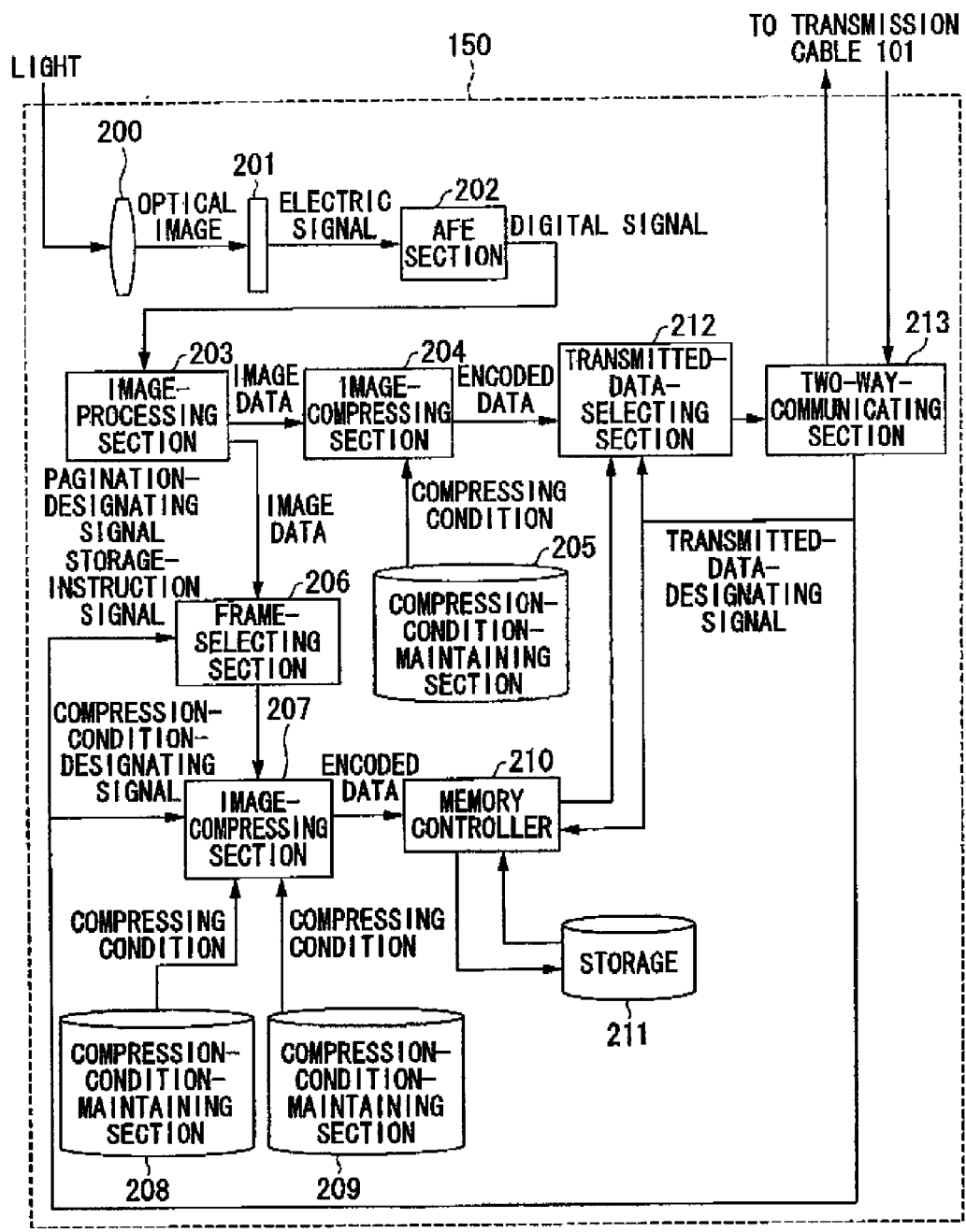
FIG. 2 is a block diagram showing the configuration of the image-pickup apparatus according to the further embodiment of the preset invention.

An image-pickup apparatus will be explained in detail next as a part of an element constituting the surveillance camera 100. FIG. 2 illustrates the configuration inside of an image-pickup apparatus 150. The image-pickup apparatus 150 has a lens unit 200, an image-pickup device 201, an AFE section 202, an image-processing section 203, an image-compressing section 204, a compression-condition-maintaining section 205, frame-selecting section 206, an image-compressing section 207, compression-condition-maintaining sections 208 and 209, a memory controller 210, a storage 211, a transmitted-data-selecting section 212, and a two-way-communicating section 213.

The lens unit 200 receives an optical image incident thereinto and emits it onto the image-pickup device 201. The lens unit 200 consists of a plurality of lenses, and actuators for mechanically moving the lenses so as to provide an optical zooming function and to compensate aberrations. The image-pickup device 201, typically a charge-coupled device (CCD) and a complementary metal oxide semiconductor (CMOS), receives the two-dimensional optical image formed by means of the lens unit 200 and converts the image into an electric signal.

A color filter transmissive with respect to specific color light is applied on the front surface of the image-pickup device 201, which is provided with a plurality of two-dimensional plane photosensitive elements for converting the received optical image into an electric signal as shown in FIG. 3. The color filter has color-filtering regions each corresponding to one specific color, i.e., R indicative of red, G indicative of green, and B indicative of blue per each front surface of the photosensitive element applied thereon as shown in FIG. 3.

One electric signal is generated by one photosensitive element in one session of image pickup. One frame of the image is constituted by a collection of electric signals generated by a plurality of photosensitive elements. The image size is determined based on the number of the photosensitive elements disposed on a two-dimensional plane.

Repeating of image pickup at a predetermined time interval provides the framed image data corresponding to the time interval. A viewer can view a moving image by means of the monitor 103, which displays the image based on the image data obtained at the time interval. Meanwhile, the present embodiment will be explained based on the presupposition that an electric signal is successively read and generated by the image-pickup device 201 per every frame of processing using a progressive scan method as shown in FIG. 4A. An interlacing method for processing every field by means of interlaced-scanning as shown in FIG. 4B can also be applicable to the present embodiment.

The AFE section 202 converts the analogue electric signal generated by the image-pickup device 201 into a digital signal for use as an image data. The AFE section 202 is constituted by a double sampling (CDS) circuit for eliminating noise, an automatic-gain-control (AGC) circuit for processing an analogue signal, and an A/D converter for converting an analogue signal into a digital signal.

The image-processing section 203 improves the quality of a signal indicative of an image data converted by the AFE section 202 or converts the signal indicative of an image data into a format associated with the following processes. Conducted for extending the obtained definition are, e.g., pixel-defect compensation, pixel interpolation using other colors, and distortion-compensating. Also, in order to improve the efficiency of the following image-processing process, the image-compressing section 203 converts an RGB format image data into a YUV format image data by executing the following equations. It should be noted that the above-explained image processing can be omitted if necessary.

$$Y=0.299 \times R+0.587 \times G+0.114 \times B$$

$$V=0.500 \times R-0.419 \times G-0.081 \times B+128$$

$$U=-0.169 \times R-0.331 \times G+0.500 \times B+128$$

Image-compressing sections 204 and 207, and compression-condition-maintaining sections 205, 208, and 209 will be explained next in detail. In a case where the amount of image data obtained by the image-pickup device 201 at every unit time is equal to or greater than a bit rate of a transmitting path through which the image data is transmitted, not all of the image data can be transmitted. To address this case, an image-compressing process provides a reduced amount of image data so that the obtained image data having the adjusted bit rate can be transmitted by the transmitting path.

The transmissible bit rate of a transmitting path is as follows in a case where a VGA image has 640 pixels by 480 pixels in size, a frame rate indicating the number of shots per every second is 30 fps, and a bit rate of the a transmitting path is 10 Mbps:

$$640 \times 480 \times 8 \text{ bit(contrast)} \times 3 \text{ planes(YUV space)} \times 30\text{fps} \approx 221\text{Mbps}$$

$$221\text{Mbps} \div 10\text{Mbps} = 22.1$$

Therefore, the data amount must be less than $1/23$ by means of image-compressing process. In addition, the significant capacity of the storage 211 can be spared by conducting the image-compressing process onto an image data subject to be stored in the storage 211 although the image quality is slightly deteriorated.

The method, which will be explained as the presupposition of the present embodiment, for compressing and encoding an image data is the JPEG method. The compressing and encoding processes using the JPEG method are constituted of frequency-conversion, quantization, and variable-length encoding. The frequency-conversion process divides an image data frame into 8 pixels in longitude by 8 pixels in latitude of blocks; executes discrete cosine transform (DCT) onto each block in order to obtain a frequency resolution.

The components each having been frequency-resolved in the frequency-conversion process are divided in the quantization process by a value based on a quantization table. The reducible amount of data and the degree of image deterioration depend on the magnitude of the value in the quantization table. In the variable-length-encoding process, redundant parts of image data are deleted by conducting Huffman encoding onto each quantized component so that an element having greater probability of occurrence is converted into a somewhat shorter encoded data, and an element having lower probability of occurrence is converted into a somewhat longer encoded data.

These are the explanations concerning the processes conducted based on the JPEG method. In addition, the image-compressing process conducted in the image-compressing sections 204 and 207 is not limited to the above JPEG method, that is, the MPEG method, JPEG2000 method, and pixel-sub-sampling method are applicable to the image-pickup apparatus according to the present invention.

The frequency-conversion, quantization, and variable-length-encoding process conducted byte variable-length-encoding process are based on the quantization table maintained in the compression-condition-maintaining section 205. The processes conducted by the image-compressing section 207 are based on the quantization table maintained in one of the compression-condition-maintaining sections 208 and 209. The process conducted by the image-compressing section 207 is based on a compression-condition-designating signal (reducing-method-designating information) output from a two-way-communication section 213. The image-compressing section 204 deletes the amount of image data in view of the bit rate of a transmitting path. The image-compressing section 207 saves the capacity of the storage 211 by reducing the amount of the image data stored in the storage 211. It should be noted that the image-compressing section 207 is not an indispensable feature. The image-compressing section 204 compresses and encodes an image data which has picked up a moving object by a compression rate higher than that of the image-compressing section 207 so that the image data of the moving object is adapted for real-time transmission. The image-compressing section 207 compresses and encodes a still image data by a compression rate lower than that of the image-compressing section 204 so as to obtain a high quality image data.

The compression-condition-maintaining sections 205, 208, and 209 are constituted by static random access memories (SRAMs), etc. These compression-condition-maintaining sections 205, 208, and 209 maintain not only the quantization table but also information specific for the JPEG method, e.g., image size and a restart marker. A header indicating the information including the quantization table is added to a generated encoded data. The compressing conditions maintained in the compression-condition-maintaining sections 208 and 209 are different from each other because the image-compressing section 207 selects a desirable one of the compressing conditions and encodes an image data based on the compression condition-designating signal. It should be noted that the compressing condition may be fixed. The encoded data transmitted by the image-pickup apparatus 150 is received by the data-processing apparatus 102 shown in FIG. 1, which recognized the header added to the received encoded data subject to be decompressed and decoded.

Details of the frame-selecting section 206 will be explained next. The frame-selecting section 206 selects an image data subject to be stored in the storage 211 from the image data output by the image-processing section 203. The operations of the frame-selecting section 206 are controlled by a storage-instruction signal (stored-data-designating information) and a pagination-designating signal that are output by the two-way-communicating section 213. The storage-instruction signal indicates the image data subjects to be stored in the storage 211. The pagination-designating signal indicates the number of image data subjects to be stored in the storage 211. In a case where the pagination-designating signal designates a plurality of image data, the designated number of consecutive image data frames are stored in the storage 211.

Figure 5:
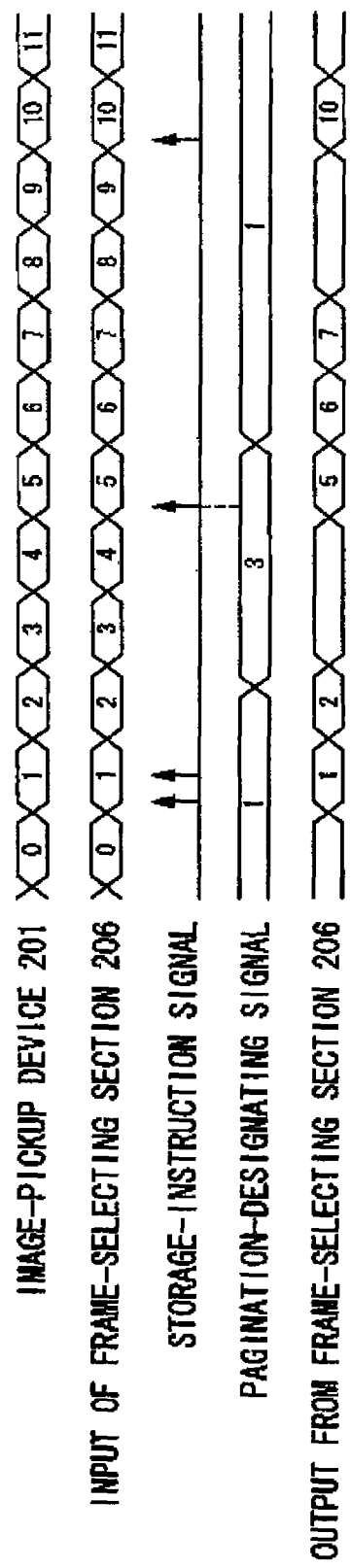
FIG. 5 is a timing diagram for illustrating operations conducted by a frame-selecting section provided to the image-pickup apparatus according to the first embodiment of the present invention.

The timing diagram illustrated in FIG. 5 indicates how the frame-selecting section 206 selects the image data with respect to each frame. Element used in the time charts illustrated in the drawings including FIG. 5 hereafter will be defined as follows. A numeric value N (N is an integer) described in the timing diagrams indicates the frame having an image data currently under the image-processing. Meanwhile, a numeric value described in a line of the pagination-designating signal indicates the number of image data to be successively stored in the storage 211 based on the indication obtained from the frame-selecting section 206. For example, the image-pickup device 201 conducts a photoelectric conversion process onto a frame 1 at a timing "1" indicated in the line of the image-pickup device 201. In addition, the frame-selecting section 206, etc., does not conduct specific processes at timings where nothing is indicated.

In a case where the pagination-designating signal in addition to the storage-instruction signal are output from the two-way-communicating section 213, the frame-selecting section 206, upon detecting the storage-instruction signal, outputs the corresponding number of image data frames designed by the pagination-designating signal whether or not the storage-instruction signal exists in the succeeding frames. As shown in FIG. 5, the frame-selecting section 206 outputs the image data corresponding to the frames 1, 2, 5, 6, 7, and 10 based on the storage-instruction signal and the pagination-designating signal. For example, three frames including the frames 5, 6, and 7 are effective since the storage-instruction signal is detected and the pagination-designating signal indicates "3" at a time corresponding to the frame 5; and the frame-selecting section 206 outputs the image data corresponding to each frame to the image-compressing section 207. Furthermore, the next frame indicated as N+1 is effective in a case where a storage-instruction signal is detected while an image data of a certain frame N is input into the frame-selecting section 206.

Details of the memory controller 210, the storage 211, and the transmitted-data-selecting section 212 will be explained next. The memory controller 210 writes an encoded data of the frame selected by the frame-selecting section 206 into the storage 211 and reads the encoded data stored in the storage 211. The memory controller 210 generates control signals, e.g., an enabling signal and an address signal corresponding to the storage 211. When the storage 21 receives a command to read out the data stored in the storage 211 based on a transmitted-data-designating signal (transmitted-data-designating information) which is output from the two-way-communicating section 213, the memory controller 210 stops writing of the encoded data into the storage 211 and starts reading out the corresponding data from a start-address of the storage 211.

The storage 211 constituted by, e.g., a volatile SRAM, a dynamic random access memory (DRAM), or a non-volatile flash memory stores the encoded data based on the control signal output from the memory controller 210.

The transmitted-data-selecting section 212 selects one of the encoded data output from the image-compressing section 204 and the encoded data output from the memory controller 210 and outputs the selected encoded data to the two-way-communicating section 213. The outputs from the image-compressing section 204 and the memory controller 210 are switched by the transmitted-data-selecting section 212 based on the transmitted-data-designating signal output from the two-way-communicating section 213.

The two-way-communicating section 213 transmits the encoded data output from the transmitted-data-selecting section 212 to the data-processing apparatus 102 as shown in FIG. 1 through the transmitting path for transmission use. Also, the two-way-communicating section 213 receives the electric signal from the data-processing apparatus 102 through a transmitting path for reception use and outputs the received electric signal to the elements disposed in the image-pickup apparatus in order to set operation modes of the elements. Signals prepared for setting the operation modes in the present embodiment are a storage-instruction signal, a pagination-designating signal, a compression-condition-designating signal, and a transmitted-data-designating signal. The two-way-communicating section 213 receives these signals from the data-processing apparatus 102 and outputs as follows: the storage-instruction signal and the pagination-designating signal are output to the frame-selecting section 206; the compression-condition-designating signal is output to the image-compressing section 207; and the transmitted-data-designating signal is output to the memory controller 210 and to the transmitted-data-selecting section 212.

The data-processing apparatus 102 shown FIG. 1 records and stores the encoded data output from the image-pickup apparatus 150, decompresses and decodes the encode data by a decompressing method corresponding to the compressing method used in the image-compressing sections 204 and 207, and shows images on a monitor.

Figure 6:
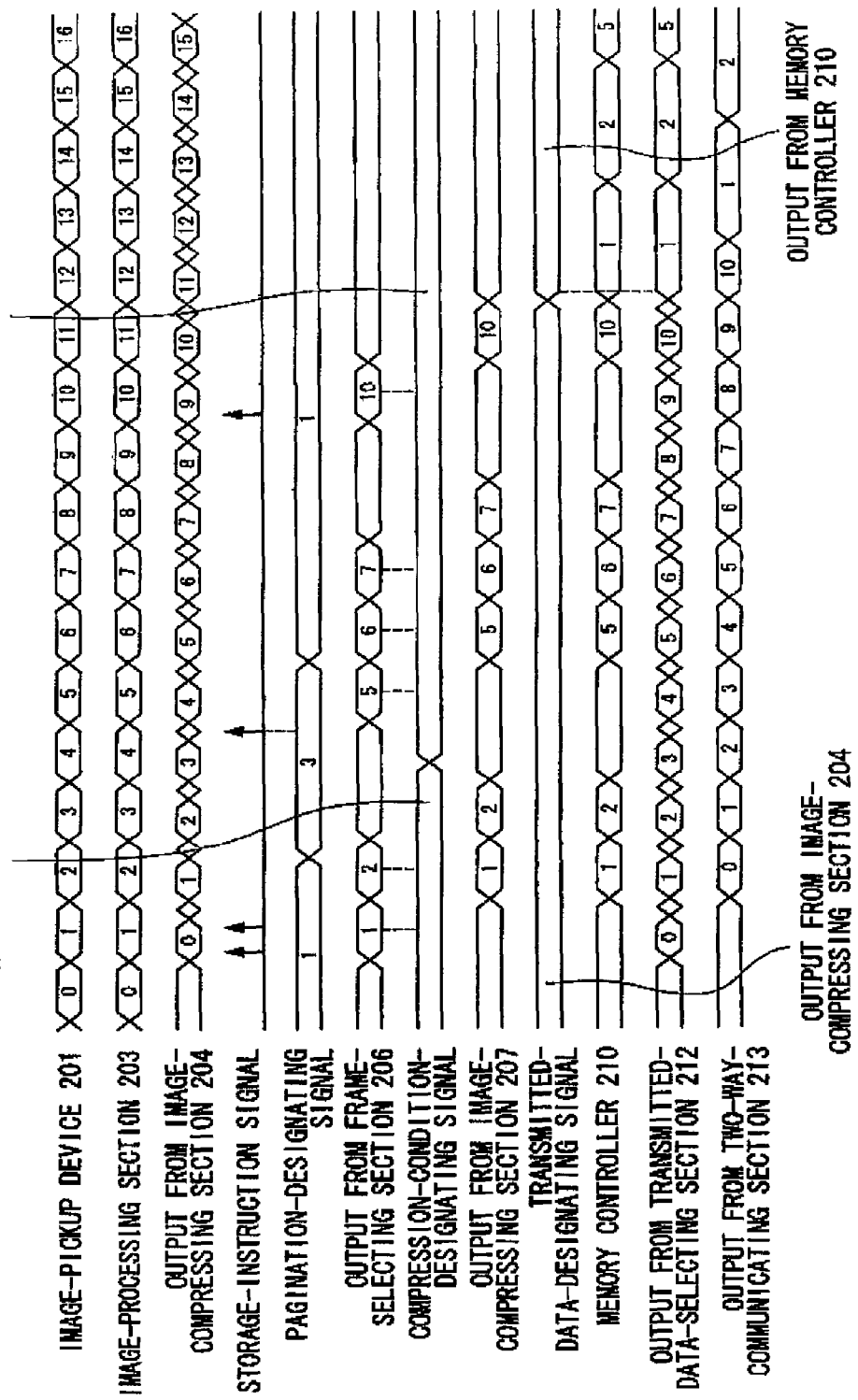
FIG. 6 is a timing diagram showing the operation conducted by the image-pickup apparatus according to the first embodiment of the present invention.

Next an explanation will be provided as to when the image-compressing section 207, the memory controller 210, the transmitted-data-selecting section 212, and the two-way-communicating section 213 will be operated in the above-explained image-pickup apparatus 150. A timing diagram shown in FIG. 6 provides information as to when the elements in the image-pickup apparatus 150 will be operated. The image data output from the frame-selecting section 206 is compressed and encoded by the image-compressing section 207 based on a quantization table maintained in the compression-condition-maintaining section designated by the compression-condition-designating signal.

That is, the image data corresponding to the frames 1 and 2 are compressed and encoded using the quantization table maintained in the compression-condition-maintaining section 208, and the image data corresponding to the frames 5, 6, 7, and 10 are compressed and encoded using the quantization table maintained in the compression-condition-maintaining section 209. The memory controller 210 writes the image data into the storage 211 when the transmitted-data-designating signal designates the output from the image-compressing section 204 and reads out the image data from the storage 211 when the transmitted-data-designating signal designates the output from the memory controller 210.

That is, the memory controller 210 writes the image data corresponding to the frames 1, 2, 5, 6, 7, and 10 into the storage 211 during the period in which the transmitted-data-designating signal designates the output from the image-compressing section 204. Also, the memory controller 210 reads out the image data written in the storage 211 corresponding to the frames successively during a period in which the transmitted-data-designating signal designates the output from the memory controller 210.

The transmitted-data-selecting section 212 switches the encoded data output from the image-compressing section 204 and the encoded data output from the memory controller 210 based on the designation indicated by the transmitted-data-designating signal and outputs the switched encoded data. The bit rate of the encoded data input into the two-way-communicating section 213 is adjusted corresponding to the bit rate of the transmitting path, and the adjusted encoded data is transmitted to a transmission cable 101. A time required for picking up one frame of image and a time required for transmitting the picked up image are identical with respect to the encoded data that is output from the image-compressing section 204 to the two-way-communicating section 213.

The storage-instruction signal, the pagination-designating signal, the compression-condition-designating signal, and the transmitted-data-designating signal that are transmitted from the data-processing apparatus 102 shown in FIG. 1 are received by the two-way-communicating section 213. These signals generated by the data-processing apparatus 102 are based on the operations carried out by a surveillant using the operation unit 105. For example, the surveillant monitoring the image displayed on the monitor 103 may provide various instructions with respect to the image data stored in the storage 211 at desirable moments, namely, when to store, the number of images to be stored, and the compressing condition. This configuration provides the image data compressed and encoded based on the condition designated by the surveillant and stored the storage 211.

Also, the image data subject to transmission may be designated at a predetermined moment in a case where the surveillant wishes to identify the image data stored in the storage 211. Accordingly, the image data stored in the storage 211 is transmitted from the two-way-communicating section 213 to the data-processing apparatus 102, which records the image data, or the monitor 103 displays the image.

As described above, the image data obtained by the image-pickup device 201 in the image-pickup apparatus 150 according to the present embodiment is compressed and encoded by the image-compressing section 204 so as to be adjusted to the bit rate of the transmitting path, and the adjusted image data is transmitted to an apparatus in the exterior thereof by the two-way-communicating section 213. Also, the image data selected by the frame-selecting section 206 and compressed and encoded by the image-compressing section 207 is stored in the storage 211. When a certain frame of image data is obtained by the image-pickup device 201 and stored in the storage 211, the same frame of image data is transmitted to the apparatus in the exterior thereof by the two-way-communicating section 213. Since both the image data having a higher frame rate suitable for a motion image and the high quality image suitable for a still image can be obtained in such a frame, two different quality image data can be obtained.

Also, since the image-compressing section 204 according to the present embodiment compresses and encodes image data and reduces the amount of image data to be transmitted from the two-way-communicating section 213, the adjusted amount of image data can be transmitted through a transmitting path having a limited bit rate. Also, since the frame-selecting section 206 selects image data to be stored in the storage 211 by every frame, the capacity of the storage 211 can be saved. Furthermore, since the image data subject to be stored in the storage 211 is selected by the frame-selecting section 206 based on the storage-instruction signal received from the apparatus in the exterior thereof, the high quality image data can be stored in the storage 211 as the time desirable for the operator of the apparatus in the exterior thereof.

Also, the frame-selecting section 206 according to the present embodiment stores the successive frames of image data based on the pagination designated by the pagination-designating signal and on the instruction provided by the storage-instruction signal to select image data. This configuration allows the storage 211 to store plural frames of image data at one time of storage.

Also, since the compression-condition-designating signal according to the present embodiment sets how to reduce the amount of each image data to be stored in the storage 211, image quality can be set according to the significance of the image data.

Also, the transmitted-data-selecting section 212 according to the present embodiment selects one of the image data output from the image-compressing section 204 and the image data stored in the storage 211 and outputs the selected image data to the two-way-communicating section 213. Accordingly, the image data stored in the storage 211 is transmitted to the exterior apparatus so that the exterior apparatus may use the received image data for recording use or for displaying use. Also, the exterior apparatus can obtain both the image data having a high frame rate suitable for a real-time-moving image and the high quality still image data suitable for viewing use since bit rate of the transmitting path may not have to be considered in view of transmitting the image data stored in the storage 211 to the exterior apparatus. Furthermore, the high quality image data can be transmitted to the exterior apparatus at an arbitrary time required by an operator of the exterior apparatus since the transmitted-data-selecting section 212 selects the image data based on the transmitted-data-designating signal.

Although the image data stored in the storage 211 is transmitted to the exterior apparatus through the transmitting path in the present embodiment, how to transmit the image data from the storage 211 to the exterior apparatus is not limited to this configuration using the transmission cable 101. For example, in another configuration, the storage 211 detachable from the image-pickup apparatus 150 may be connected to the exterior apparatus so as to obtain the image data from the storage 211 directly.

The surveillant show in FIG. 1 can conduct a real-time-monitoring of the motion image displayed on the monitor 103 disposed in a surveillance camera system using the image-pickup apparatus of the present embodiment, and if something unidentified is displayed on the monitor 103, the surveillant can obtain a high quality image thereof by operating the operation unit 105. The surveillance camera system may have a further advantageous feature in that the image of the unidentified object may be printed out for evidence.

Figure 7:
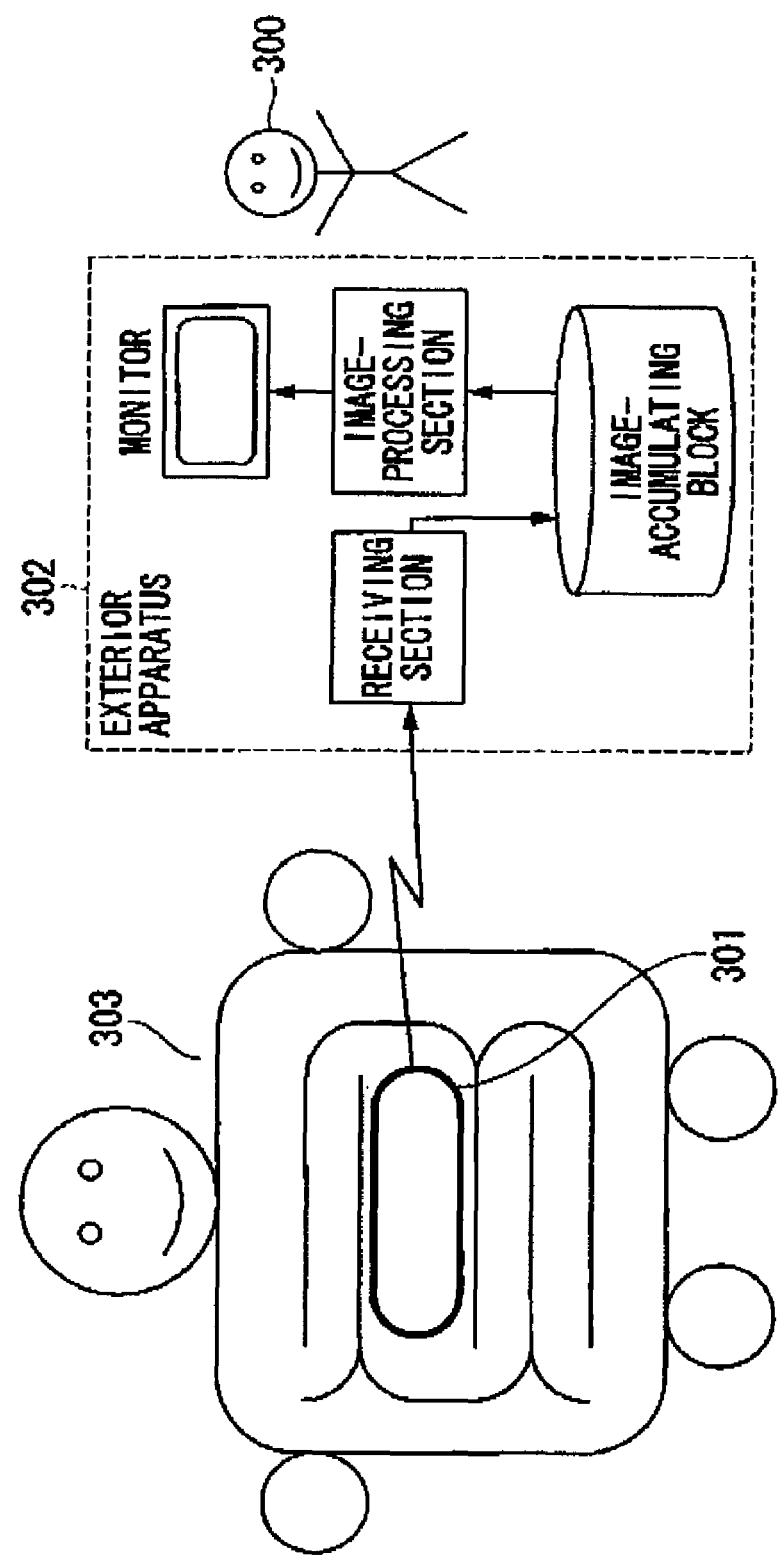
FIG. 7 is a schematic view of a capsule endoscope system according to a second embodiment of the present invention.

A second embodiment of the present invention will be explained with reference to an example of an image-pickup apparatus of the present invention applied to a capsule endoscope system. FIG. 7 is a schematic diagram of the capsule endoscope system according to the present embodiment. As shown in FIG. 7, diagnosis and treatment are carried inside the body of a patient 303 by a doctor 300 using the capsule endoscope system constituted by a capsule endoscope 301 and an exterior apparatus 302.

The patient 303 first swallows the capsule endoscope 301. A battery for driving various inner modules and a wireless transmission antenna are built in the capsule endoscope 301 for picking up an image of the inside of the patient, body and transmitting the picked up image data to the exterior apparatus 302 trough the wireless transmission antenna. A data-processing 302 conducts predetermined data-processing on the image data transmitted from the capsule endoscope 301. After that, the processed image data is stored or displayed on a monitor. The diagnosis and treatment are conducted by the doctor 300 after observing the image displayed on the monitor or recorded therein.

Figure 8:
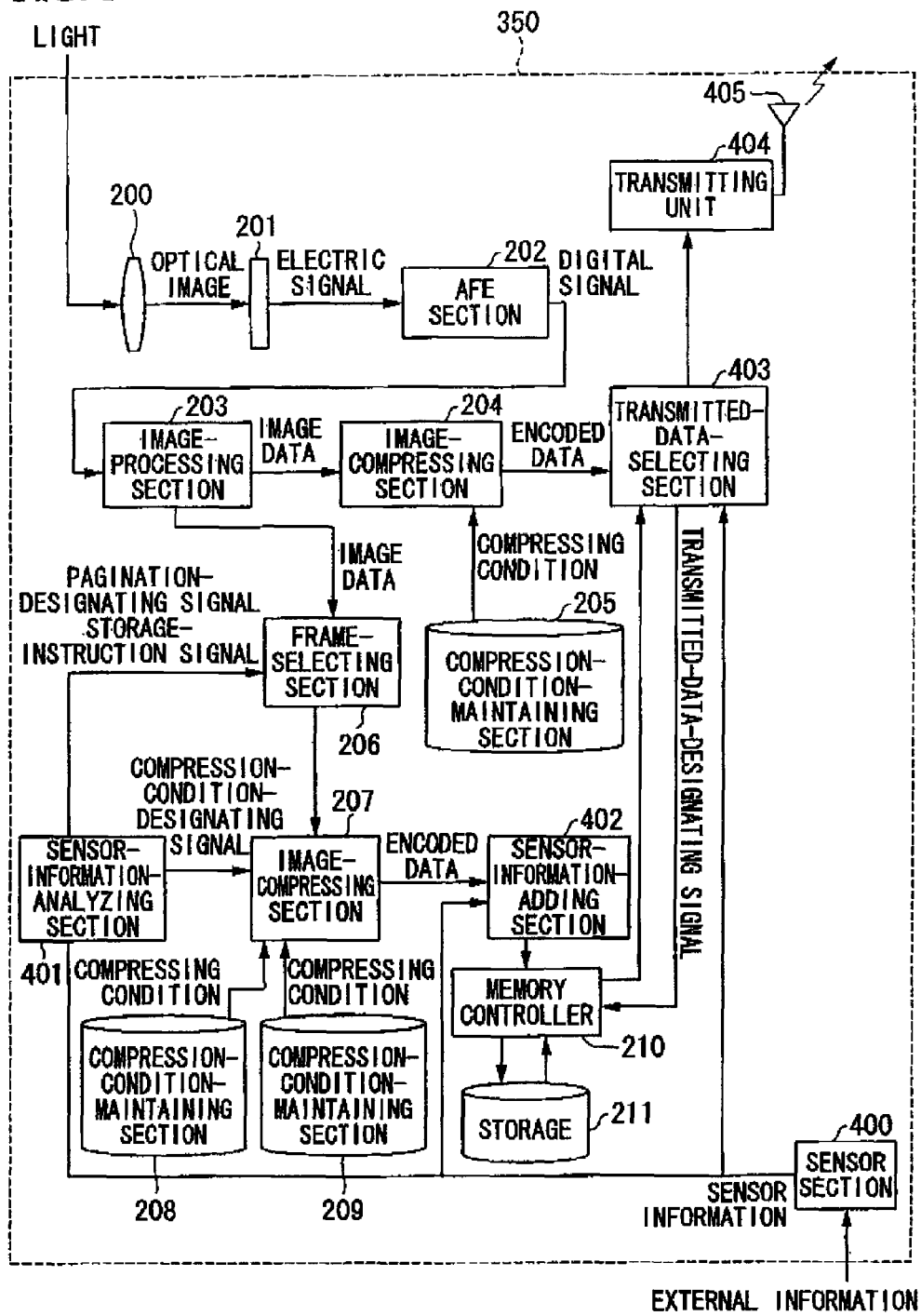
FIG. 8 is a block diagram showing the configuration of the image-pickup apparatus according to the second embodiment of the present invention.

An image-pickup apparatus will be explained next in detail as a part of an element constituting the capsule endoscope 301 according to the present embodiment. FIG. 8 illustrates the configuration inside of an image-pickup apparatus 350. The same reference numerals are added to the elements having the same functions as those illustrated in FIG. 2 so as to omit the explanation of duplicated features; thus, only different features will be explained hereafter. The image-pickup apparatus 350 shown in FIG. 8 is characterized by a sensor section 400, a sensor-information-analyzing section 401, a sensor-information-adding section 402, a transmitted-data-selecting section 403, and a transmitting section 404.

Figure 9:
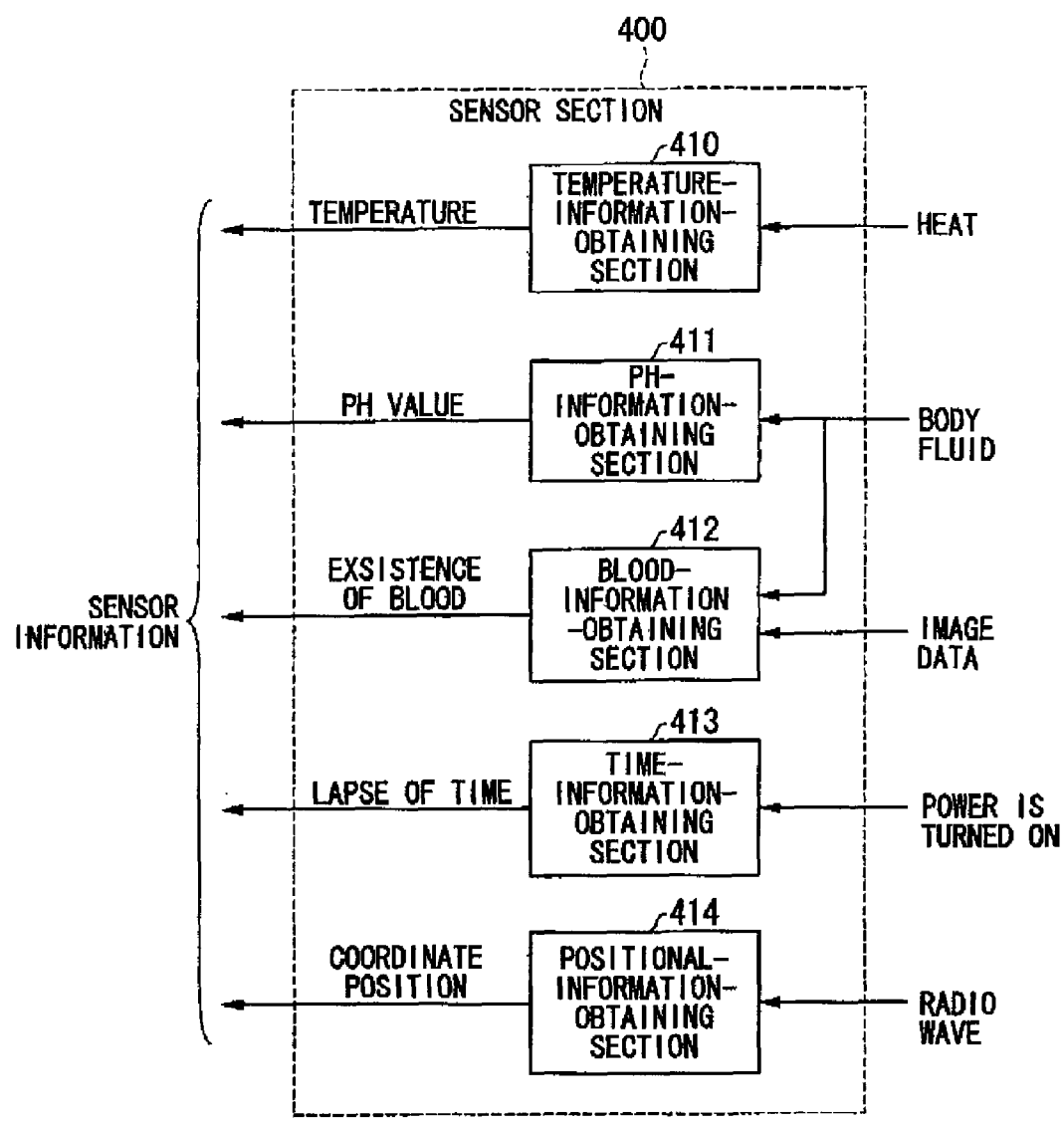
FIG. 9 is a block diagram showing the configuration of sensor sections provided to the image-pickup apparatus according to the second embodiment of the present invention.

The sensor section 400 constituted by sensors disposed inside the image-pickup apparatus 350 obtains various types of information, e.g., relating to the outside of the image-pickup apparatus 350. FIG. 9 illustrates the configuration inside of the sensor section 400. The sensor section 400 has a temperature-information-obtaining section 410, a pH-information-obtaining section 411, a blood-information-obtaining section 412, a time-information-obtaining section 413, and a positional-information-obtaining section 414.

The temperature-information-obtaining section 410 obtains temperature information indicative of an exterior of to image-pickup apparatus 350 (inside of the body into which the image-pickup apparatus 350 is inserted). To be more specific, the temperature-information-obtaining section 410 is constituted by transistors having an amplifying function similar to a temperature sensor system disclosed in Japanese Unexamined Patent Application, First Publication No. H6-213730 in which temperature is calculated based on the time required for obtaining a predetermined current value by applying voltage onto a gate electrode.

The pH-information-obtaining section 411 calculates a pH-value indicative of hydrogen ion concentration (acidity/alkalinity) from sampled body fluid. The pH-value may be calculated by using various commonly-known pH-detecting apparatuses.

The blood-information-obtaining section 412 obtains information indicative of whether or not bleeding exists outside the image-pickup apparatus 350. To be more specific, the blood-information-obtaining section 412 having a section for storing luminol in an aqueous solution and an image-pickup module for obtaining luminance information mixes the sampled body fluid and the luminol in an aqueous solution, and based on the luminance value of the temporarily-picked up image data, to blood-information-obtaining section 412 determines whether or not bleeding exists.

Also, the blood-information-obtaining section 412 extracts image data indicative of a red in color from the image data obtained by the image-pickup device 201, and based on a color distribution of the image data indicative of a red in color, the blood-information section 412 determines whether or not bleeding exists. The blood-information-obtaining section 412 outputs the information, indicative of whether or not bleeding exists, which is based on the result of the OR operation obtained from information indicative of a luminance of a mixture of a luminol in an aqueous solution and the body fluid; and color distribution of the image indicative of a red in color. The value indicative of luminance is calculated based on the image data obtained by the image-pickup module, and the luminance value is compared with a threshold are compared in the case of determining whether or not bleeding exists based on the luminance information of the mixture of luminol in an aqueous solution and the body fluid. If the luminance value is greater than the threshold, the determination indicates the existence of bleeding.

The time-information-obtaining section 413 is constituted by a counter circuit operative based on a flag generated by turning the image-pickup apparatus 350 on. The value incremented by the counter circuit, i.e., the lapse of time is output by the time-information-obtaining section 413. The positional-information-obtaining section 414 having a plurality of antennae for receiving the corresponding number of frequency bands calculates the coordinate position of the image-pickup apparatus 350 based on time differences among the times indicating when the corresponding number of radio waves emitted by the exterior apparatus at the same moment as each other will be received by the positional-information-obtaining section 414.

The information obtained by the above sensing elements is output in a lot. Various type of information obtained by the sensor section 400 are not limited to the above configuration. Any component that obtain beneficial information may be adapted in the image-pickup apparatus 350.

The sensor-information-analyzing section 401 analyzes the sensor information and generates a pagination-designating signal and a storage-instruction signal for selecting the image data to be stored in the storage 211. The sensor-information-analyzing section 401 also generates a compression-condition-designating signal for instructing compressing and encoding conditions conducted by the image-compressing section 207. The storage-instruction signal instructs that the image data be stored in the cases where bleeding is detected based on the sensor information or where the image-pickup apparatus 350 reaches the specific point subject to diagnosis. On this occasion, the compression-condition-designating signal and pagination-designating signal instruct the compressing condition, e.g., lowering the compression ratio in a case where bleeding is detected, and pagination of the image data according to significance of the image.

Figure 10:
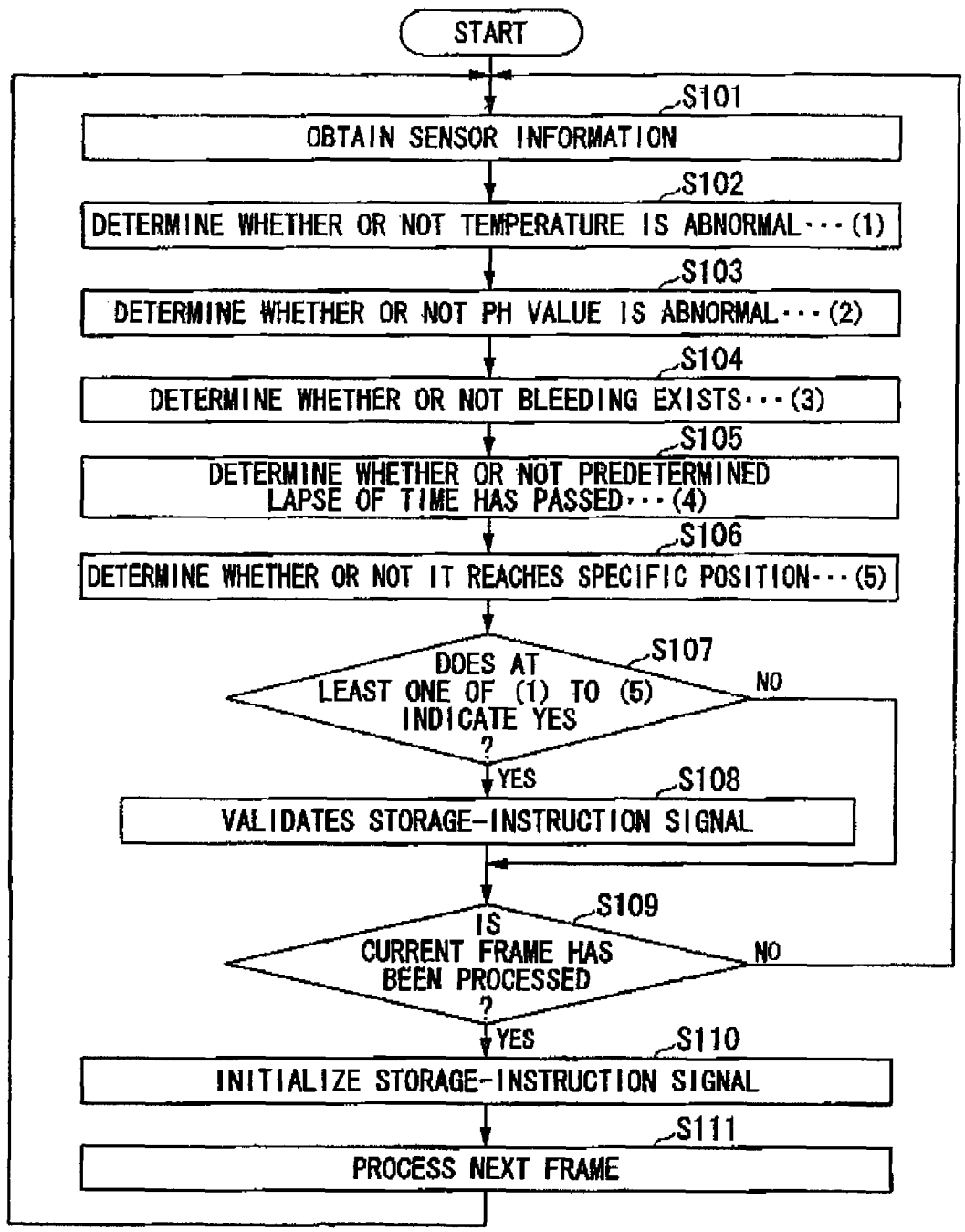
FIG. 10 is a flow chart block diagram showing the configuration of a sensor-information-analyzing section provided to the image-pickup apparatus for illustrating operations conducted by a sensor-information-analyzing section provided to the image-pickup apparatus according to the second embodiment of the present invention.
Figure 11:
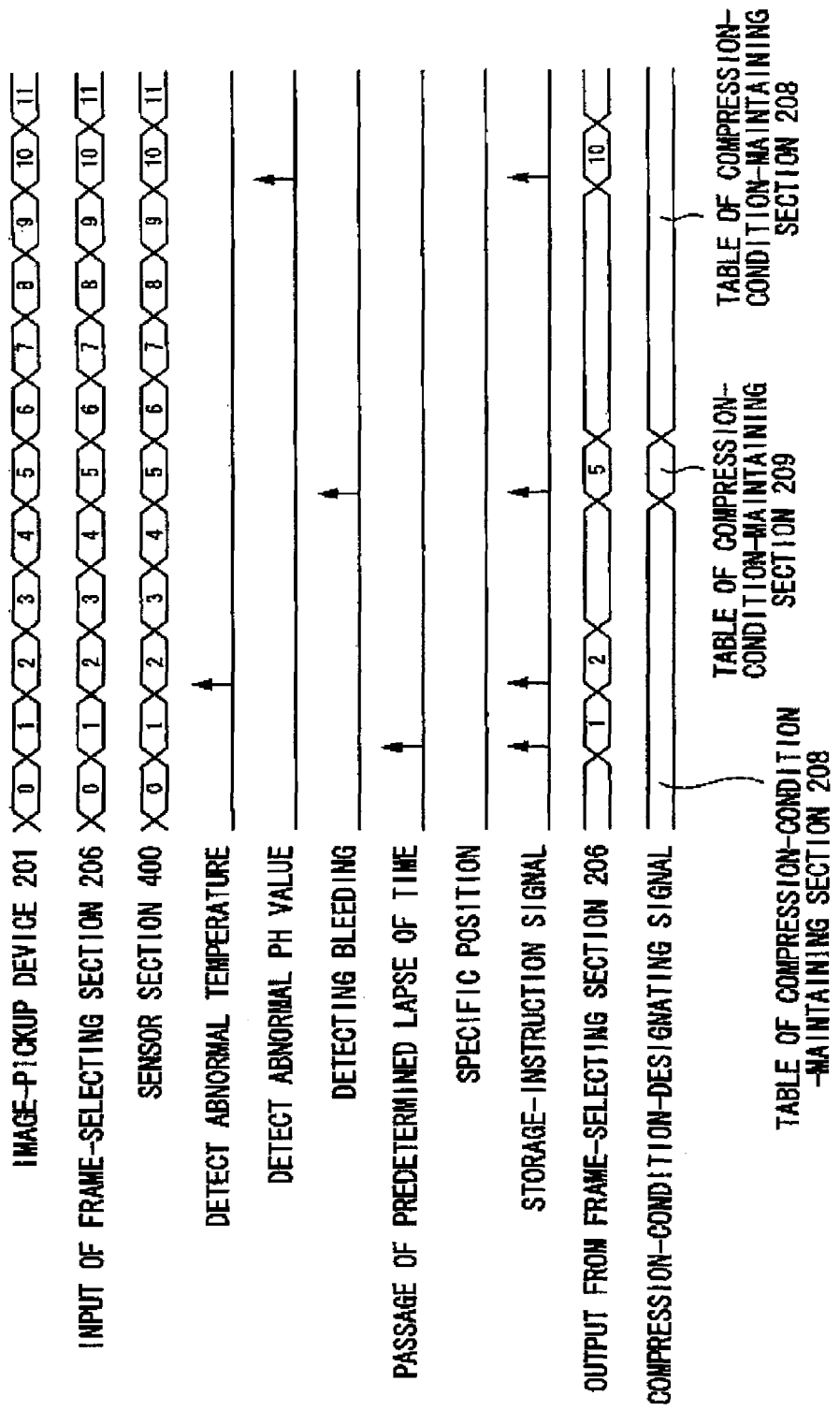
FIG. 11 is a timing diagram for illustrating operations conducted by the frame-selecting section provided to the image-pickup apparatus according to the second embodiment of the present invention.

The operations conducted by the sensor-information-analyzing section 401 will be explained as follows with reference to FIGS. 10 and 11. FIG. 10 is a flow chart of the procedure determines whether or not the image data should be stored in the storage 211. FIG. 11 is a timing diagram that describes how the frame-selecting section 206 selects the image data.

As shown in FIG. 10, the consecutive determinations conducted by the sensor-information-analyzing section 401 having obtained the sensor information from the sensor section 400 (step S101) are whether or not temperature is abnormal; whether or the pH-value is abnormal; whether or not bleeding exists; whether or not a predetermined period of time has passed; and whether or not the image-pickup apparatus 350 has reached the specific position (steps S102 to S106). The steps S102 to S106 are not limited to this order, i.e., the steps may be in an arbitrary order.

The sensor-information-analyzing section 401 subsequently determines whether at least one of the above steps has identified an abnormality in temperature or pH-value, bleeding, lapse of time, the access to the specific position (step S107) based on the determination results obtained in the steps S102 to S106. The produce proceeds to a step S108 in a case where at least one of the items is identified, and the procedure proceeds to a step S109 in a case where no item is identified.

The sensor-information-analyzing section 401 validates the storage-instruction signal subject to be output to the frame-selecting section 206 in the step S108. This configuration allows the frame-selecting section 206 to select the image data corresponding to the frame where some abnormality or a specific condition is detected. The sensor-information-analyzing section 401 subsequently determines in the step S109 whether or not the processing of the currently-executed frame has finished. The procedure returns to the step S101 in a case where the processing of the currently-executed frame has not finished. Also, the sensor-information-analyzing section 401 initializes the storage-instruction signal (step S110) in a case where the processing of the currently-executed frame has finished and deems that the procedure should proceed to the next step (step S111). The procedure subsequently returns to the step S101.

As shown in FIG. 11, the storage-instruction signal is generated based on the logical sum (OR operation) of results with respect to an abnormality in temperature, abnormality in pH-value, detection of bleeding, lapse of time, and position of the image-pickup apparatus.

It is therefore revealed that the image data of frame 2 is selected based on the abnormality in temperature, the image data of frame 10 is selected based on the abnormality in pH-value, the image data of frame 5 is selected based on detection of bleeding, and the image data of frame 1 is selected based on detection of a predetermined lapse of time. The frame-selecting section 206 outputs the image data corresponding to the frames 1, 2, 5 and 10 based on the storage-instruction signal.

The sensor-information-adding section 402 adds the information output from the sensing elements of the sensor section 400 to the encoded data corresponding to the frame selected by the frame-selecting section 206. That is, the information indicative of the temperate, the pH-value, existence of bleeding, and the coordinate position, which has been used by the sensor-information-analyzing section 401 for determining whether or not the image data is selected is added to the encoded data. The sensor information added to the end data corresponding to the selected frame is obtained at the same time as that when the image data of the corresponding frame is obtained by the image-pickup device 201.

Figure 12:
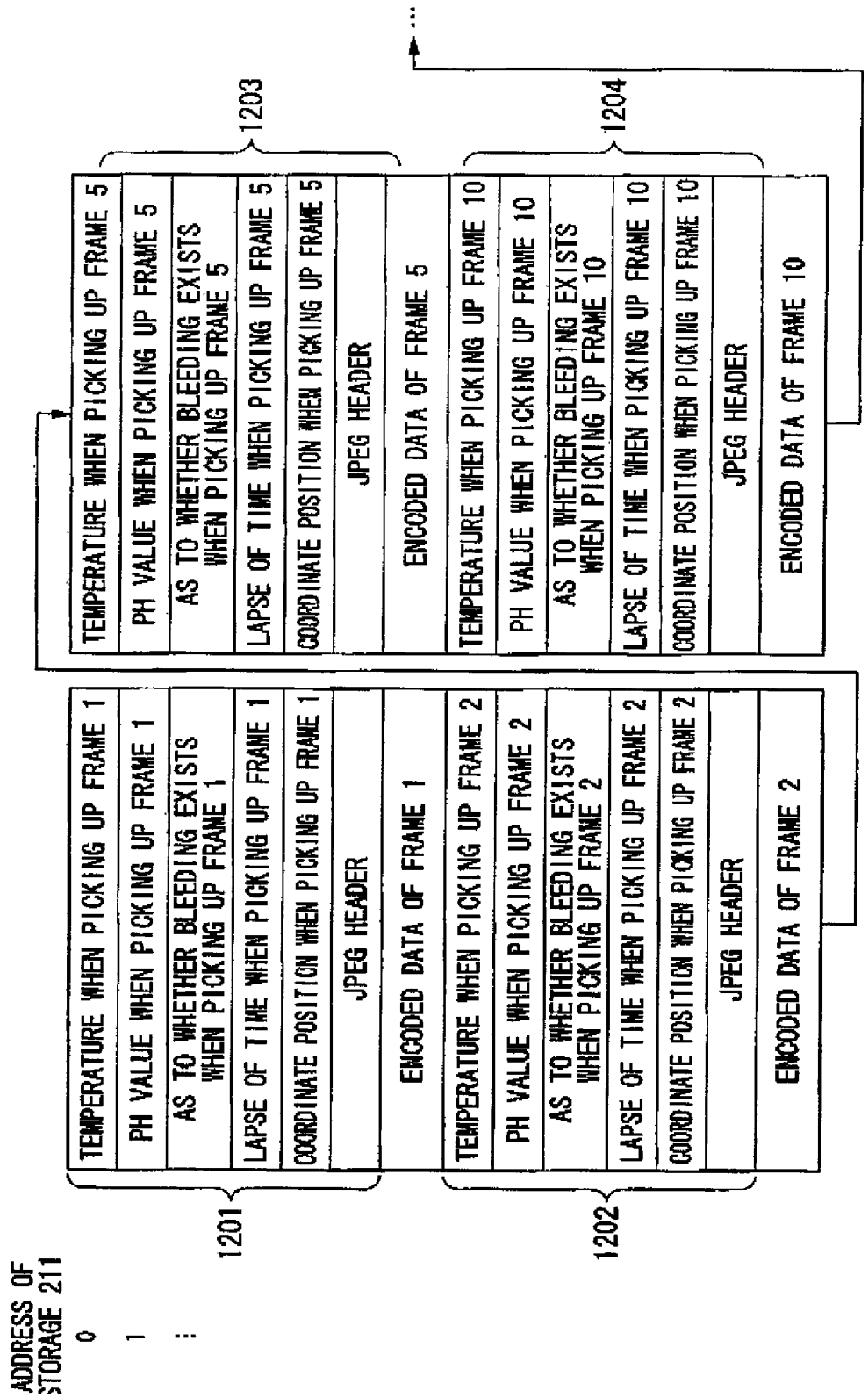
FIG. 12 shows the structure of data stored in a storage section provided to the image-pickup apparatus according to the second embodiment of the present invention.

The structure of data stored in the storage 211 is illustrated in FIG. 12 based on the timing diagram shown in FIG. 11. The information obtained from to sensor section 400 is added to headers (headers 1201, 1202, 1203, and 1204 based on the example shown in FIG. 12) of the encoded data per frame and stored in the storage 211. The exterior apparatus 302 conducts predetermined processing on the information added by the sensor-information-adding section 402. The information used hereby and obtained from the sensor section 400 conveys the state of the inner body picked up in the frame selected by the frame-selecting section 206 to the doctor 300.

The transmitted-data-selecting section 403 analyzes the sensor information output from the sensor section 400 and outputs a transmitted-data-designating signal to the memory controller 210. The transmitted-data-selecting section 403 selects one of the encoded data output from the image-compressing section 204 and the encoded data output from the memory controller 210 and outputs the selected encoded data to the transmitting section 404. The transmitted-data-selecting section 403 outputs the transmitted-data-designating signal to the memory controller 210 and instructs it to read the encoded data from the storage 211 in a case where the output from the memory controller 210 is selected.

The transmitted-data-designating signal generated based on the sensor information output from the sensor section 400 is used for determining as to which one of the image-compressing section 204 and the memory controller 210 the encoded data output to the exterior apparatus 302 should be obtained from. The portion being picked up is specified based on the pH-value, the lapse of time, and the coordinate position of the capsule endoscope system, and the transmitted-data-designating signal is adapted so that the encoded data obtained from the image-compressing section 204 is output in a case where the portion is subject to diagnosis and that the encoded data obtained from the memory controller 210 is output in a case where the portion is not subject to diagnosis. The encoded data read out from the storage 211 is adapted to be output to the exterior apparatus 302 since the requirement for a motion image is not so significant except for the portion subject to diagnosis.

The transmitting section 404 transmits the encoded data output from the transmitted-data-selecting section 403 to the exterior apparatus 302 shown in FIG. 7 through a wireless transmission antenna 405. The communicating method used in the image-pickup apparatus according to the present invention is not limited to wireless communication although the present embodiment has been explained with reference to the capsule endoscope system that conducts wireless data transmission. The transmitting path used for outputting the encoded data from the transmitting section 404 may be either wired transmission or wireless transmission.

Figure 13:
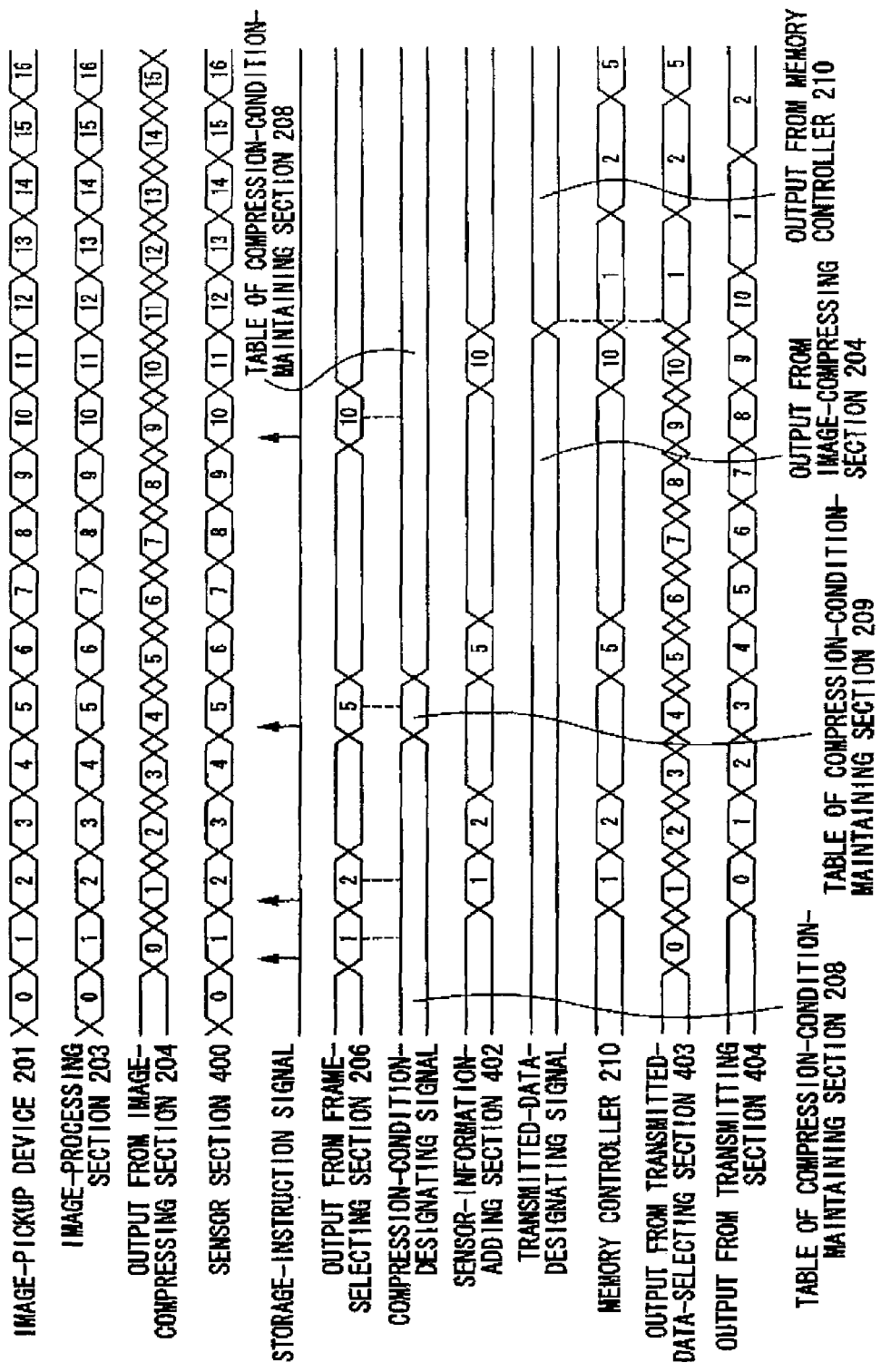
FIG. 13 is a timing diagram showing the operation conducted by the image-pickup apparatus according to the second embodiment of the present invention.

Next, an explanation will be given as to when the sensor section 400, the sensor-information-adding section 402, the memory controller 210, the transmitted-data-selecting section 403, and the transmitting section 404 will be operated in the above-explained image-pickup apparatus 350. A timing diagram shown in FIG. 13 explains as to when the elements in the image-pickup apparatus 350 will be operated. The operation of the storage-instruction signal shown in FIG. 13 will be omitted here since it has been previously explained.

The sensor section 400 obtains the sensor information per frame at the same time as the image-pickup device 201 obtains the image data. The transmitted-data-selecting section 403 switches the encoded data output from the image-compressing section 204 and the encoded data output from the memory controller 210 based on the designation indicated by the transmitted-data-designating signal and outputs the switched encoded data. The transmitting section 404 adjusts the bit rate of the encoded data corresponding to the bit rate of the transmitting path similarly to the two-way-communicating section 213 shown in FIG. 2, and outputs the encoded data.

The sensor section 400 in the image-pickup apparatus 350 according to the present embodiment obtains the sensor information at the same time as when the image-pickup device 201 obtains the image data, i.e., at the time of picking up the image. The frame-selecting section 206 selects the image data subject to be stored in the storage 211 based on the sensor information obtained from the sensor section 400. This configuration permits the image-pickup apparatus 350 to automatically select the image data subject to be stored in the storage 211 without receiving such a request from the exterior apparatus.

Also, the exterior apparatus can obtain not only high quality image data but also useful information indicative of, e.g., the state of the picked up portion in accordance with the present embodiment since the sensor-information-adding section 402 adds the sensor information obtained from the sensor section 400 onto the image data selected by the frame-selecting section 206.

Also, the transmitted-data-selecting section 403 in view of the sensor information obtained from the sensor section 400 according to the present embodiment selects one of the image data (encoded data) output from the image-compressing section 204 and the image data (encoded data) stored in the storage 211 and outputs the selected image data to the transmitting section 404. This configuration permits the image-pickup apparatus 350 to automatically transmit high quality image data suitable for a still image for viewing use to the exterior apparatus without receiving such a request.

Since the image-pickup apparatus 350 according to the present embodiment is applied to the capsule endoscope system, the doctor 300 illustrated in FIG. 7 using the capsule endoscope system can clearly recognize the motion image displayed on the monitor of the exterior apparatus 302; thus, real-time diagnosis can be conducted. The capsule endoscope system is more advantageous since it realizes a capability of obtaining information including a high quality image of the inside of the patient's body.

Similarly to the first embodiment, the method for outputting the image data from the storage 211 to the storage 211 is not limited to the above methods in the present embodiment. For instance, the exterior apparatus may be adapted to obtain the image data from the storage 211 after the image-pickup apparatus 350 is removed from a patient's body.

A third embodiment of the present invention will be explained with reference to an example of the image-pickup apparatus of the present invention applied to a capsule endoscope system similarly to the second embodiment. The schematic capsule endoscope system is almost the same configuration as that shown in FIG. 7. The configuration of the capsule endoscope 301 shown in FIG. 7 according to the present embodiment is different from that of the second embodiment in that the capsule enclosure of the capsule endoscope 301 accommodates a battery, a wireless transmission antenna, and a magnet so that a doctor 300 can operate the capsule endoscope 301 by the externally applying a magnetic force.

Figure 14:
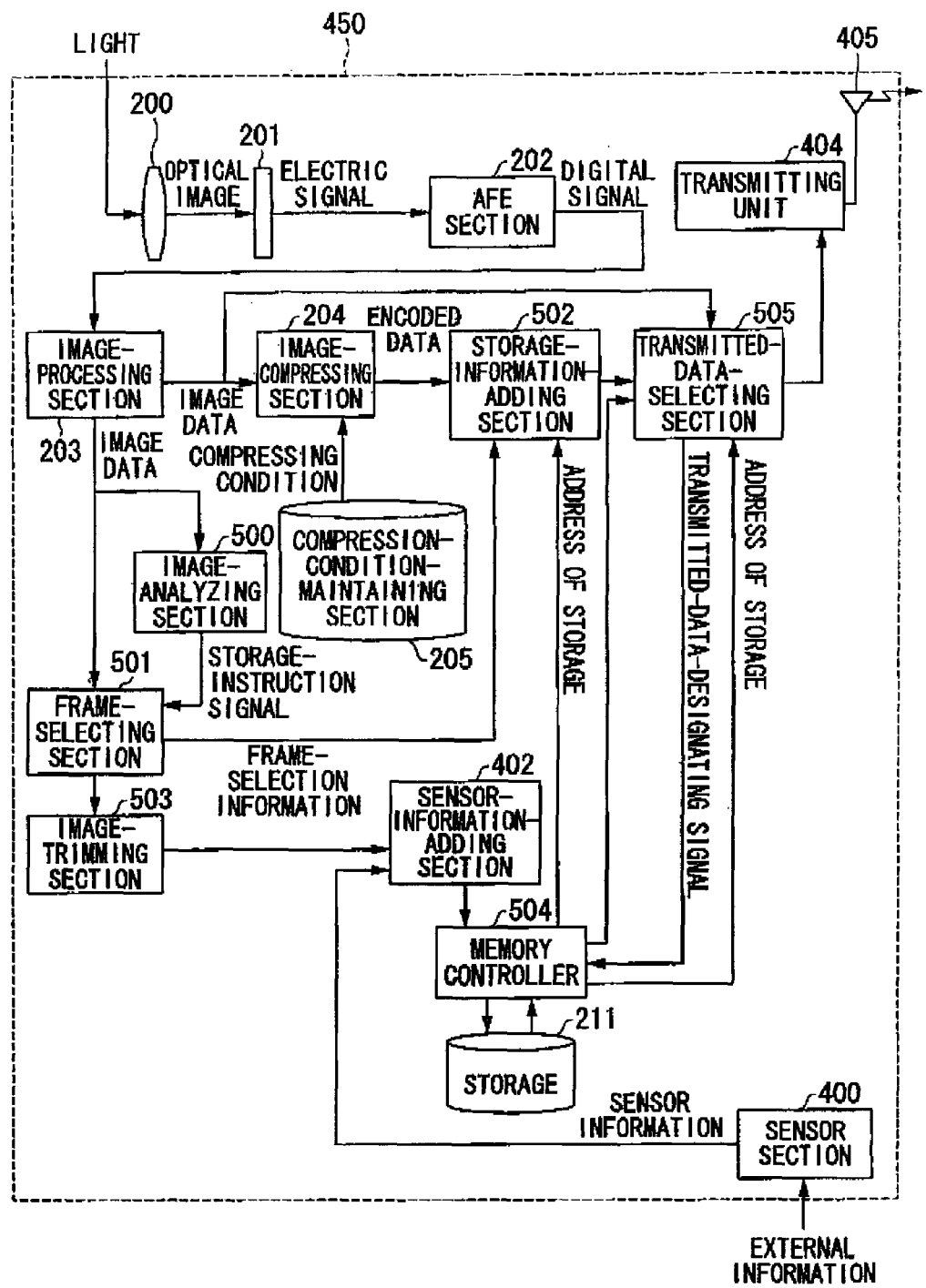
FIG. 14 is a block diagram showing the configuration of the image-pickup apparatus according to the third embodiment of the present invention.

An image-pickup apparatus will be explained as follows in detail as a part of an element constituting the capsule endoscope 301 according to the present embodiment. FIG. 14 illustrates the configuration inside of an image-pickup apparatus 450. The same reference numerals are added to the elements having the same functions as those illustrated in FIGS. 2 and 8 so as to omit explanation of the duplicated features; thus, only different features will be explained hereafter. The image-pickup apparatus 450 shown in FIG. 8 is characterized by an image-analyzing section 600, a frame-selecting section 501, a storage-information-adding section 502, an image-trimming section 503, a memory controller 504 and a transmitted-data-selecting section 505.

The image-analyzing section 600 analyzes the image data output from the image-processing section 203 and generates a storage-instruction signal indicative of the instruction as to whether or not the image data is stored in the storage 211. A method will be explained as follows for determining whether or not the image data is selected based on a motion vector detected by using a commonly known block-matching method.

Figure 15:
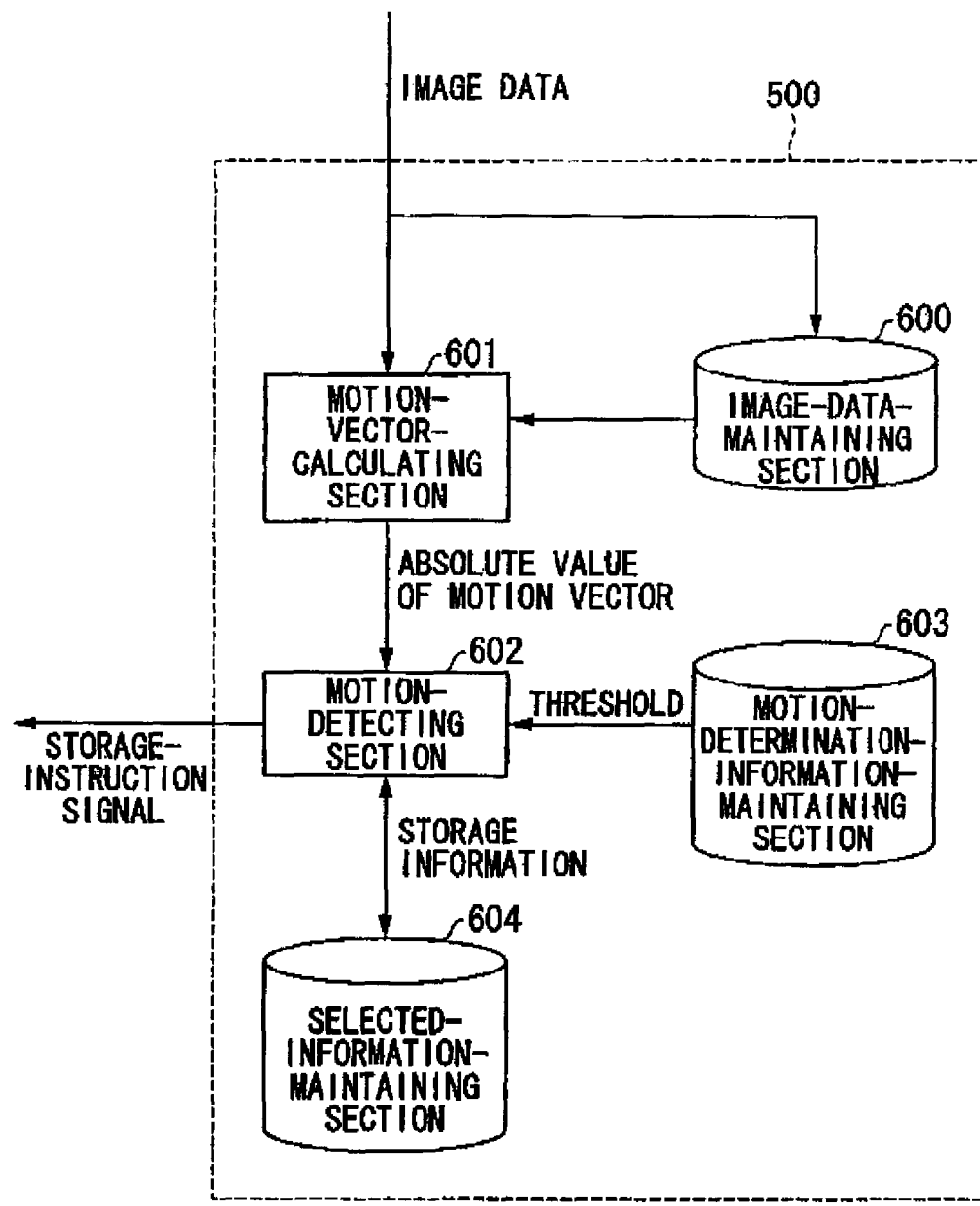
FIG. 15 is a block diagram showing the configuration of an image-analyzing section provided to the image-pickup apparatus according to the third embodiment of the present invention.
Figure 16:
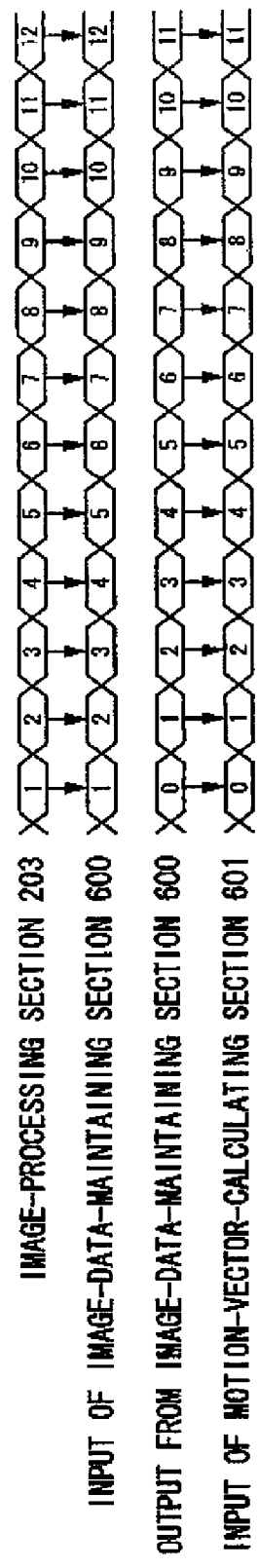
FIG. 16 is a timing diagram for illustrating operations conducted by an image-data-maintaining section provided to the image-pickup apparatus according to the third embodiment of the present invention.

An image-analyzing section shown in FIG. 15 has an image-data-maintaining section 600, a motion-vector-calculating section 601, a motion-detecting section 602, a motion-determination-information-maintaining section 603, and a selected-information-maintaining section 604. The image-data-maintaining section 600 constituted by memories, e.g., SRAMs stores one frame of image data output from the image-processing section 203. FIG. 16 is a timing diagram indicating how the image-data-maintaining section 600 maintains the image data. As shown in FIG. 2, the image-data-maintaining section 600 maintains the image data of a frame 2 output from the image-processing section 203 at the time when the image-processing section 203 conducts image-processing of the frame 2, and simultaneously, the image-data-maintaining section 600 outputs the image data of a frame 1 to the motion-vector-calculating section 601.

The motion-vector-calculating section 601 calculates the motion vector of image data output from the image-processing section 203 corresponding to the currently-processed frame subject to determine whether it is stored in the storage 211 in view of the image data corresponding to the preceding frame output from the image-data-maintaining section 600. The operations conducted by the motion-vector-calculating section 601 will be explained as follows with reference to FIGS. 17 to 20.

Figure 17:
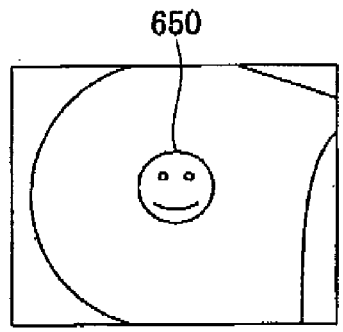
FIG. 17 is a timing diagram for illustrating operations conducted by a motion-vector-calculating section provided to the image-pickup apparatus according to the third embodiment of the present invention.
Figure 18A:
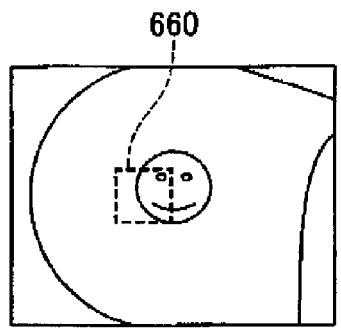
FIGS. 18A to 18C each show operations conducted by the motion-vector-calculating section provided to the image-pickup apparatus according to the third embodiment of the present invention.
Figure 18B:
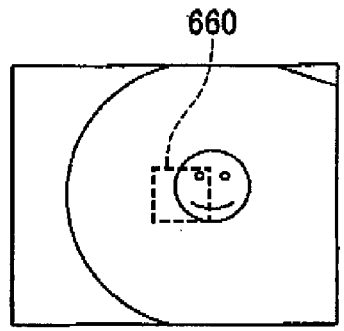
Figure 18C:
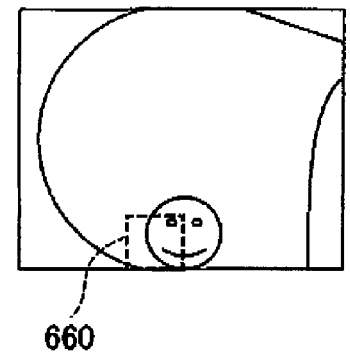

FIG. 17 illustrates an image corresponding to the frame having a motion vector subject to be calculated. FIGS. 18A to 18C illustrate three patterns for explaining an image corresponding to the preceding frame output from the image-data-maintaining section 600. Reference numeral 650 shown in FIG. 17 indicates an object subject to be picked up, and the rest of the frame indicates a background image inside of the patient's body.

Figure 19:
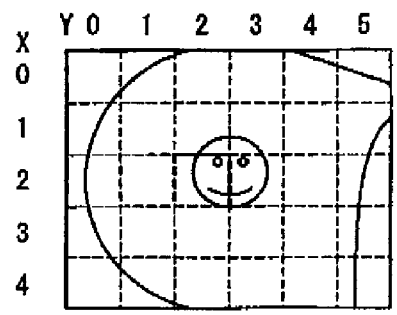
FIG. 19 shows operations conducted by the motion-vector-calculating section provided to the image-pickup apparatus according to the third embodiment of the present invention.

The image shown in FIG. 17 is first divided into block regions defined by dashed lines in FIG. 19. To facilitate the explanation hereof, each block is defined as X, Y) where X and Y are integers, X indicates longitudinal numbers with respect to the top and left-most reference block (0, 0), and Y indicates latitudinal numbers with respect to the reference block.

Following that, coincidence between each regionally-divided block and each block in the preceding frame shown in FIG. 18 is obtained. For instance, comparing the image data of the block (2, 2) shown in FIG. 19 with the image data shown in FIG. 18 reveals that the block (2, 2) is identical to the matching area 660 defined by the dashed lines shown FIG. 18. That means the block (2, 2) shown in FIG. 19 has existed in the matching area 660 in the preceding frame. The vector quantity obtained based on the current positional relationship between the block (2, 2) and the matching area 660 indicates the motion vector of block (2, 2) shown in FIG. 19.

Figure 20A:
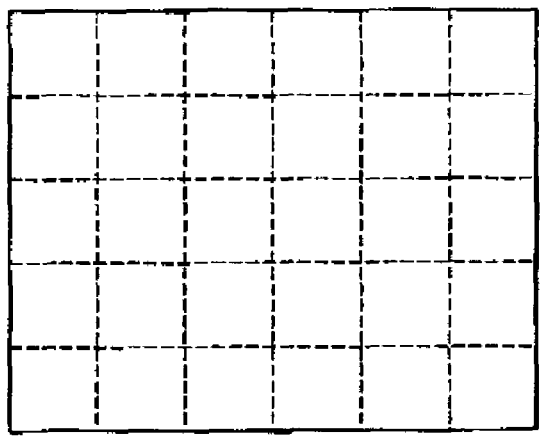
FIGS. 20A to 20C each show operations conducted by the motion-vector-calculating section provided to the image-pickup apparatus according to the third embodiment of the present invention.
Figure 20B:
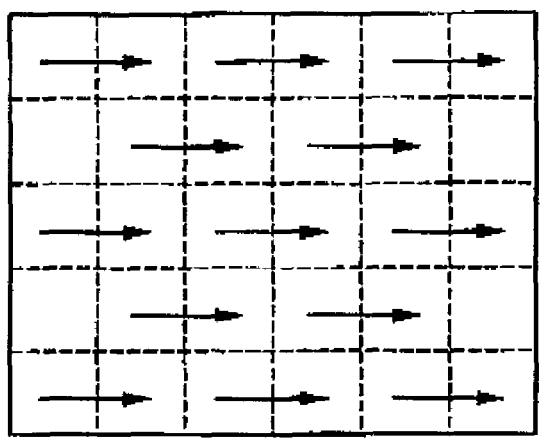
Figure 20C:
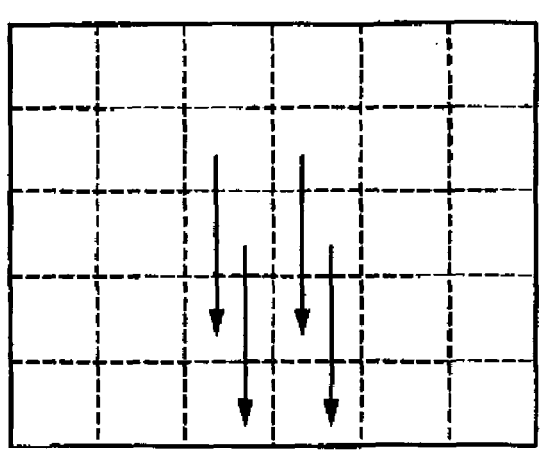

FIGS. 20A to 20C each show the motion vector obtained by conducting the above scheme onto all the blocks shown in FIG. 19. The motion-vector-calculating section 601 outputs absolute values of the motion vector illustrated in FIG. 20. The following equation yields the absolute value of the motion vector that indicates the shift from the coordinate (A2, B2) to the coordinate (A1, B1) where the coordinate of a preceding frame is (A2, B2), and the coordinate of the frame subject to calculation for obtaining the motion vector is (A1, B1):

$$\text{Absolute Value } Z \text{ of Motion Vector} = |\sqrt{(A1-A2)^2 + (B1-B2)^2}|$$

The motion-detecting section 602 compares a threshold maintained by the motion-determination-information-maintaining section 603 with the absolute value output from the motion-vector-calculating section 601 and generates the storage-instruction signal indicative of the image data stored in the storage 211. The threshold maintained by the motion-determination-information-maintaining section 603 is designated as a parameter in advance by a user. The arbitrarily adaptive threshold provides an arbitrary setting as to whether or not the storage-instruction signal is generated based on the motion detected by the motion-detecting section 602.

The explanation hereafter is based on an understanding that the threshold maintained by the motion-determination-information-maintaining section 603 is greater than zero and is not so significant (e.g., 1 (one)). The absolute values of motion vectors in all blocks in FIG. 20A are less than the threshold values maintained by the motion-determination-information-maintaining section 603, i.e., nearly zero. Since the motion vector is not detected in a monitored image if the image-pickup apparatus 450 is in a stationary state, the image-pickup apparatus 450 is presumably in a stationary state if FIG. 18A indicates a preceding frame.

The absolute values of motion vectors in all blocks in FIG. 20B are unified and more significant than the threshold values maintained by the motion-determination-information-maintaining section 603. Since mobility develops in an entire image if the image-pickup apparatus 450 moves, the image-pickup apparatus 450 is presumably guided by means of an operation if FIG. 18b indicates a preceding frame of image.

The threshold values of motion vectors in the blocks (1, 2), (1, 3), (2, 2), and (2, 3) shown in FIG. 20C exceed the threshold maintained by the motion-determination-information-maintaining section 603. The absolute values of motion vector in the other blocks are equal to or less than the threshold maintained by the motion-determination-information-maintaining section 603. Although the image-pickup apparatus 450 is in a stationary state motion vectors can be detected only in a part of the preceding frame of the image shown in FIG. 18C, the object is presumably moving.

Upon detecting the stationary state of the image-pickup apparatus 450 (i.e., when the preceding frame is indicated in FIGS. 18A and 18C), the motion-detecting section 602 outputs a storage-instruction signal indicative of storing the current frame of image data into the storage 211. That is, the storage-instruction signal indicative of storing the image data into the storage 211 is output from the motion-detecting section 602 when the absolute value of the motion vector is equal to or less than the threshold maintained by the motion-determination-information-maintaining section 603 in many existing blocks.

The motion-detecting section 602 allows the selected-information-maintaining section 604 to maintain information indicative of whether the previous frame of image data is stored in the storage 211. If the information maintained by the selected-information-maintaining section 604 indicates that the image data has been stored in the storage 211, the motion-detecting section 602 outputs a storage-instruction signal indicative of whether the frame of image subject to the detection is not stored in the storage 211 regardless of the results of the detecting motion vector.

Figure 21:
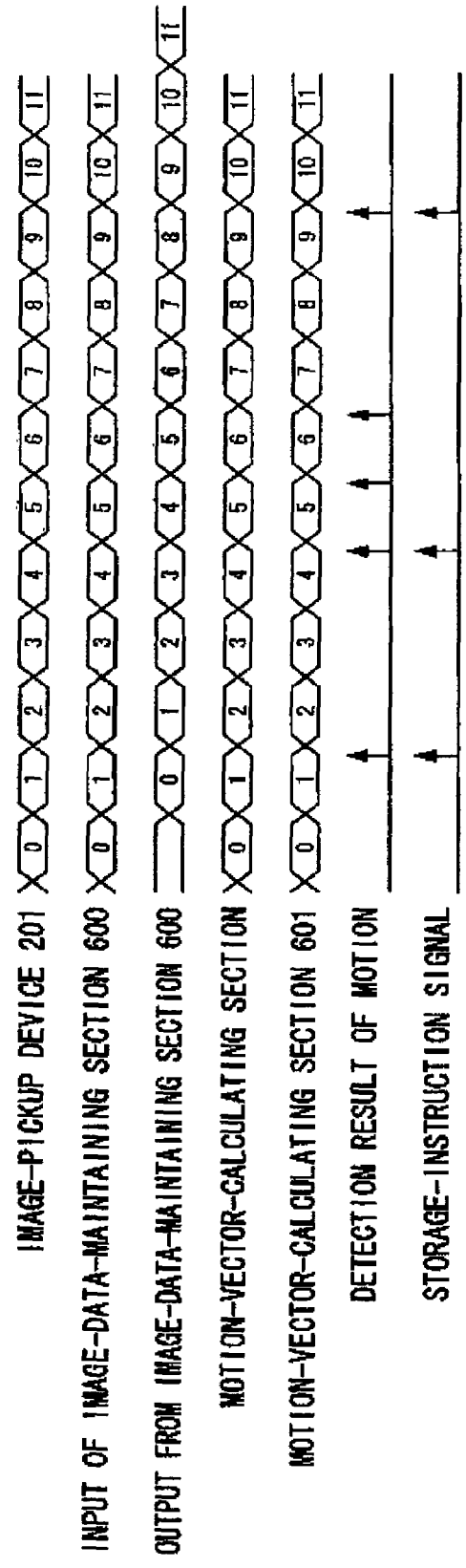
FIG. 21 is a timing diagram for illustrating operations conducted by an image-analyzing section provided to the image-pickup according to the third embodiment of the present invention.

FIG. 21 is a timing diagram indicating how a storage-instruction signal is generated by the image-analyzing section 600. The motion-vector-calculating section 601 calculates a motion vector based on a frame 0 (zero) stored in the image-data-maintaining section 600 and a frame 1 input into the motion-vector-calculating section 601 at a time when the image-pickup device 201 processes the frame 1. Whether or not the object is moving is determined by the motion-detecting section 602 based on the motion vector calculated by the motion-vector-calculating section 601; and the detection results shown in FIG. 21 reveal that an object of an image in the frames 1, 4, 5, 6, and 9 is motionless.

When the motion-detecting section 602 determines that the previous frame is motionless, i.e., the motion-detecting section 602 outputs the storage-instruction signal indicating that the previous frame of image data should be stored in the storage 211, and the next frame of image data is not stored in the storage 211 regardless of the existence of motion. As shown in FIG. 21, the storage-instruction signal is therefore output at the times indicated by the frames 1, 4, and 9, although the storage-instruction signal is not output at the times indicated by the frames 5 and 6.

Next, the frame-selecting section 501, the storage-information-adding section 502, the image-trimming section 503, the memory controller 504, and the transmitted-data-selecting section 505 will be explained in detail in this order. The frame-selecting section 501 selects an image data subject to be stored in the storage 211 from the image data output by the image-processing section 203. The operations of frame-selecting section 501 are controlled based on the storage-instruction signal output from the image-analyzing section 500. The frame-selecting section 501 also outputs frame-selection-information indicative of whether an image data is selected to the storage-information-adding section 502.

Figure 22:
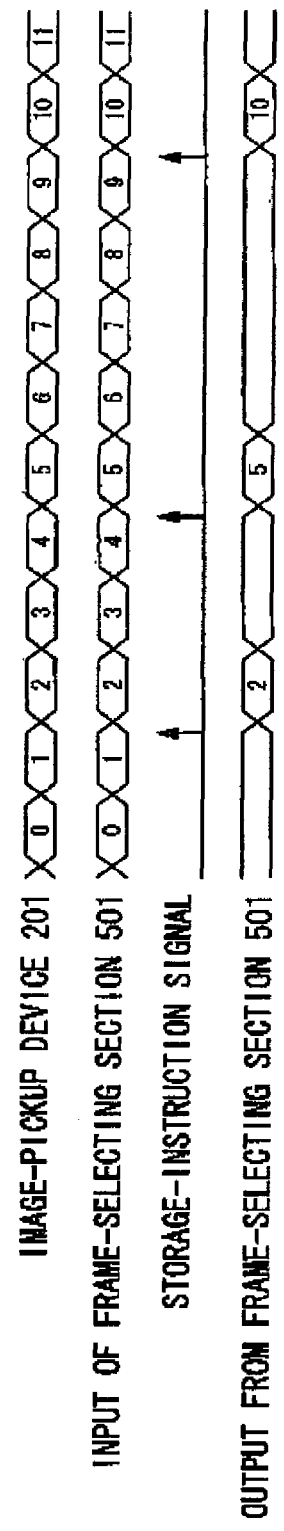
FIG. 22 is a timing diagram for illustrating operations conducted by the frame-selecting section provided to the image-pickup apparatus according to the third embodiment of the present invention.

The timing diagram illustrated in FIG. 22 indicates how the frame-selecting section 501 selects the image data. When the storage-instruction signal shown in FIG. 22 indicates that the image data corresponding to the frames 1, 4, and 9 should be stored in the storage 211, the frame-selecting section 501 outputs the image data corresponding to the frames 2, 5, and 10. The reason is as follows as to why the frame-selecting section 501 outputs the image data of frame next to the frame which the storage-instruction signal deems to be stored into the storage 211.

Whole image data in frame N must be input into the image-analyzing section 500 in order for the image-analyzing section 500 to detect motion and determine whether or not the image data in the frame N should be stored in the storage 211. A buffer for maintaining one frame of image data is required in the frame-selecting section 501 so as to store the frame N of image data in the storage 211 base on the storage-instruction signal. Whether or not the frame N+1 of image data should be stored in the storage 211 is determined by using the result of detecting the motion in the frame N of image data since the correlatively between successive frames of motion image is significant. Thus, the number of buffers herein used can be minimized while restraining errors in detection.

The storage-information-adding section 502 adds information indicative of whether a certain frame of image data is stored in the storage 211 to a header of an encoded data output from the image-compressing section 204 based on the frameselection-information output from the frame-selecting section 501. The storage-information-adding section 502 also receives an address output from the memory controller 504 and adds information indicative of the remaining capacity of the storage 211 to the header of encoded data. The remaining capacity of the storage 211 can be measured based on the address output from the memory controller 504 since the storage 211 stores the image data based on the order of address i.e., the image data having the initial address is first stored. The present embodiment is not limited to this configuration, i.e., information indicative of the remaining capacity of the storage 211 measured by the memory controller 504 may be output to the storage-information-adding section 502 and the transmitted-data-selecting section 505.

The information added by the storage-information-adding section 502 and appropriately processed by the exterior apparatus 302 is displayed on a monitor of the exterior apparatus 302. This configuration allows the doctor 300 viewing the motion image displayed on the monitor of the exterior apparatus 302 to recognize the time when the image is stored in the storage 211 and the remaining capacity of the storage 211.

The image-trimming section 503 trims the image data representing the central portion of the image data corresponding to the frame selected by the frame-selecting section 501 by removing the peripheral portion surrounding the central portion. The doctor 300 guides the image-pickup apparatus 450 used in the endoscope system using a guided capsule while observing the image displayed on the monitor of the exterior apparatus 302. The object which the doctor 300 is willing to pickup in high quality is therefore supposed to be captured in the center of the monitored image when the guided image-pickup apparatus 450 stops and the frame-selecting section 501 selects the image data subject to be stored in the stage 211. Therefore, the remaining capacity of the storage 211 can be significantly saved while the necessary image data is maintained since potentially unnecessary peripheral of the image data are removed and the central portion of image data is trimmed.

The memory controller 504 having functions similar to those of memory controller 210 shown in FIG. 2 outputs the address of the storage 211. The memory controller 504 outputs the write address of the storage 211 when the transmitted-data-designating signal indicates the output from the image-compressing section 204. The memory controller 504 outputs the read address of the storage 211 when the transmitted-data-designating signal indicates the output from the memory controller 504.

The transmitted-data-selecting section 505 has a function similar to that of the image-analyzing section 500 for obtaining the image data output from the image-processing section 203 and detecting the motion in the image. The transmitted-data-selecting section 505 selects one of the encoded data output from the image-compressing section 204 and the image data output from the memory controller 504 so as to output the selected data to the transmitting section 404 based on the result of detecting the motion vector and the remaining capacity of the storage 211 having the address output from the memory controller 504.

The transmitted-data-selecting section 505 output the transmitted-data-designating signal to the memory controller 504 and instructs it to read the image data from the storage 211 in a case where the output from the memory controller 504 is selected. Although the transmitted-data-selecting section 505 according to the present embodiment is supposed to have the function for detecting the motion in an image, the transmitted-data-selecting section 505 may obtain the result of detecting motion in the image from the image-analyzing section 500 so that the information indicative of the obtained result may be used for selecting the data subjected to transmission.

Figure 23:
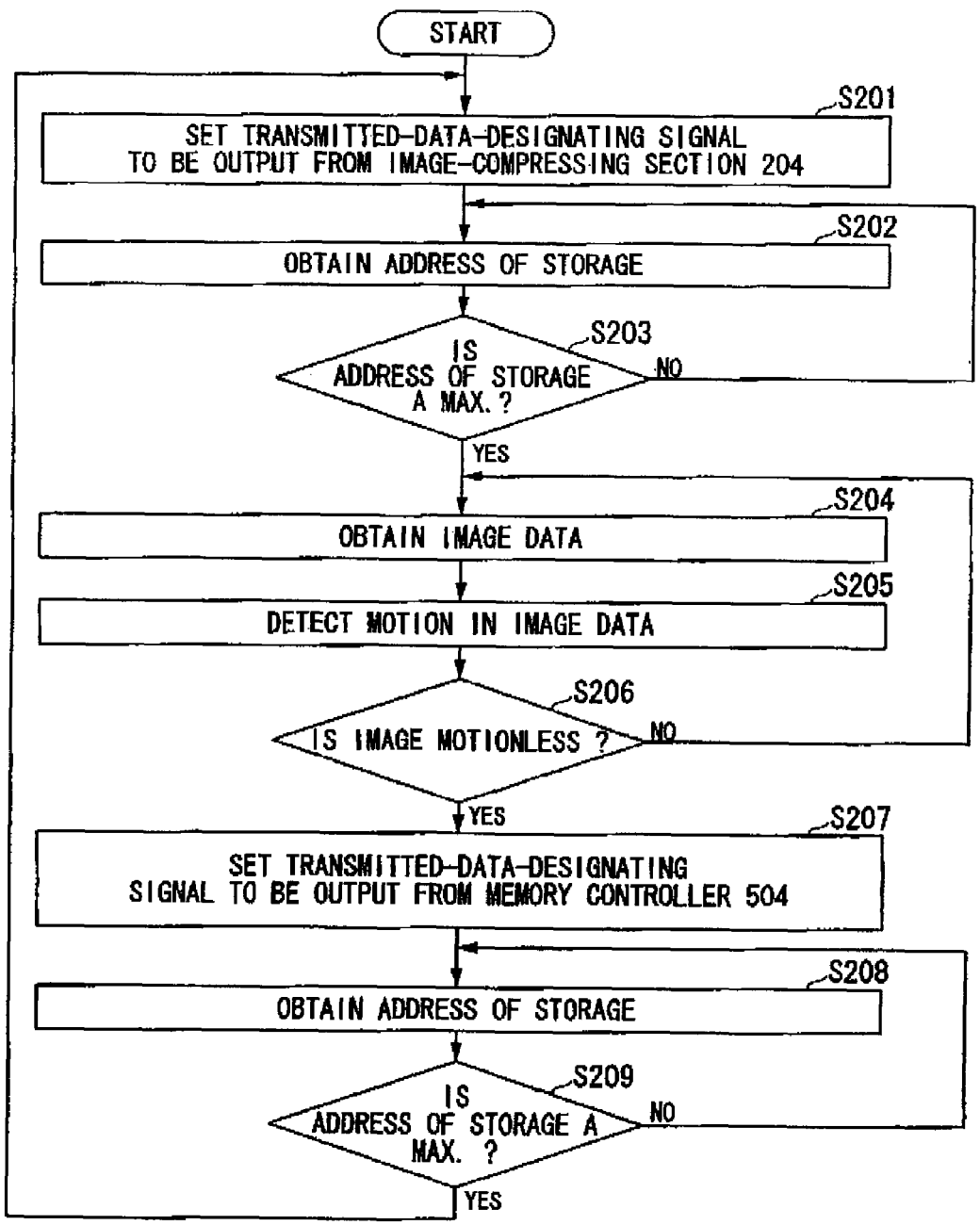
FIG. 23 is a flow chart block diagram showing an order of operations conducted by the frame-selecting section provided to the image-pickup apparatus according to the third embodiment of the present invention.

The operation of the transmitted-data-selecting section 505 for selecting data subject to transmission will be explained next with reference to FIG. 23. The flow chart shown in FIG. 23 illustrates the stepwise operations for selecting the data subject to transmission. As shown in FIG. 23, the transmitted-data-selecting section 505 sets up the transmitted-data-designating signal to be the output from image-compressing section 204 so that the motion image can be viewed in real time on the monitor of the exterior apparatus 302 shown in FIG. 7 (step S201). As previously explained, the image-pickup apparatus 450 allows the storage 211 to store the image data while the transmitted-data-designating signal is set up to be the output from the image-compressing section 204.

After that, the transmitted-data-selecting section 505 obtains the address of the storage 211 from the memory controller 504 (step S202) and determines whether or not the write address of the storage 211 reaches the preset maximum (step S203). In a case where the write address of the storage 211 is less than the maximum, the operation for storing the image data into the storage 211 continues.

The transmitted-data-selecting section 505 also obtains the image data from the image-processing section 203 (step S204) and detects motion (step S205) in a case where the write address of the storage 211 reaches the maximum. The obtaining of image data and detecting of motion are repeated in a case where the detected motion in the image exceeds a preset value ("No" in step S206). The transmitted-data-selecting section 505 sets up the transmitted-data-designating signal to be the output from the memory controller 504 (step S207) and obtains the address of the storage 211 from the memory controller 504 (step S208) in a case where the detected motion is equal to or less than the preset value, i.e., the image is motionless ("Yes" in step S206). The image data is read out from the storage 211 and transmitted while the transmitted-data-designating signal is set up to be the output from the memory controller 504.

The image data is read out from the storage 211 based on the order of address, i.e., the image data having the initial address is first read. The transmitted-data-selecting section 505 determines whether or not the read address of the storage 211 reaches the maximum (step S209). In a case where the write address of the storage 211 is less than the maximum, the operation for reading out the encoded data from the storage 211 and transmitting it continues. Also, in a case where the read address of the storage 211 is maximum, the transmitted-data-designating signal is set back to the output from the image-compressing section 204 (step S201). The operation hereafter is the same as above.

The image data stored in the storage 211 is output to the exterior apparatus 302 when the write address of the storage 211 is maximum while the operation for storing the image data into the storage 211 continues. However priority is given to displaying of the motion image on the monitor of exterior apparatus 302 while the image-pickup apparatus 450 is guided. Therefore, whether the image-pickup apparatus 450 is guided is determined by detecting the motion in the image, and the transmitted-data-designating signal is set to be the output from the memory controller 504 after observing that the image becomes motionless.

Figure 24:
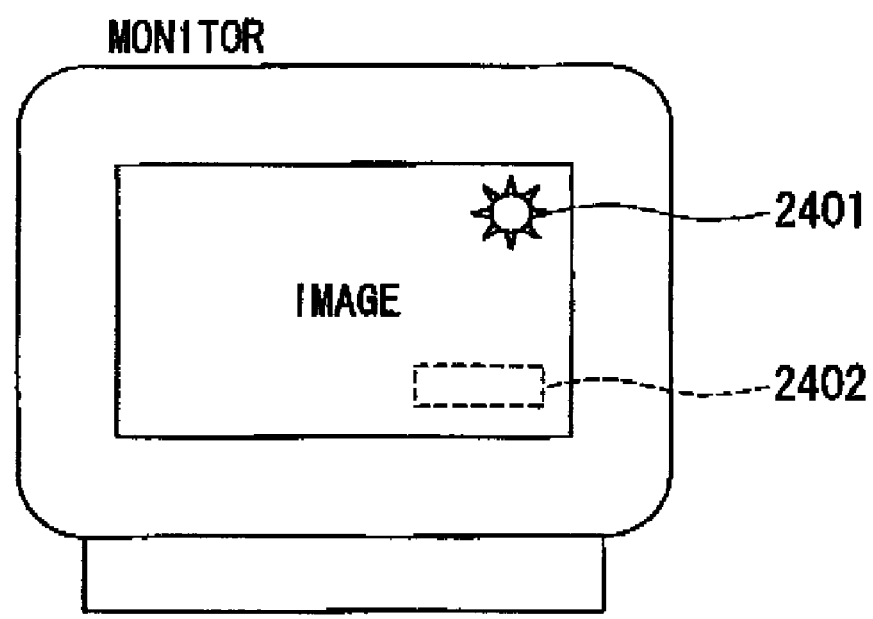
FIG. 24 shows an image displayed on a monitor of an exterior apparatus in an exterior of a human body according to the third embodiment of the present invention.

The exterior apparatus 302 conducts recording of the stored image and displays the image by using the monitor after the image data is output from the image-pickup apparatus 450 to the exterior apparatus 302 shown in FIG. 7. FIG. 24 illustrates how an image is displayed on the monitor of the exterior apparatus 302. FIG. 24 shows the image-displaying state and illustrates how the encoded data output from the image-compressing section 204 is output to the exterior 302. The exterior apparatus 302 decompresses and decodes the encoded data out from the image-pickup apparatus 450 and displays the image thereof on the monitor. The exterior apparatus 302 also detects the information (information per frame indicative of whether or not the image data is stored in the storage 211; and the information indicative of the remaining capacity of the storage 211) that is added to the encoded data by to storage-information-adding section 502 and notifies the remaining storage capacity 2402 to the storage-enclosure-notification lamp 2401 and the doctor 300, who observes the monitor.

Figure 25:
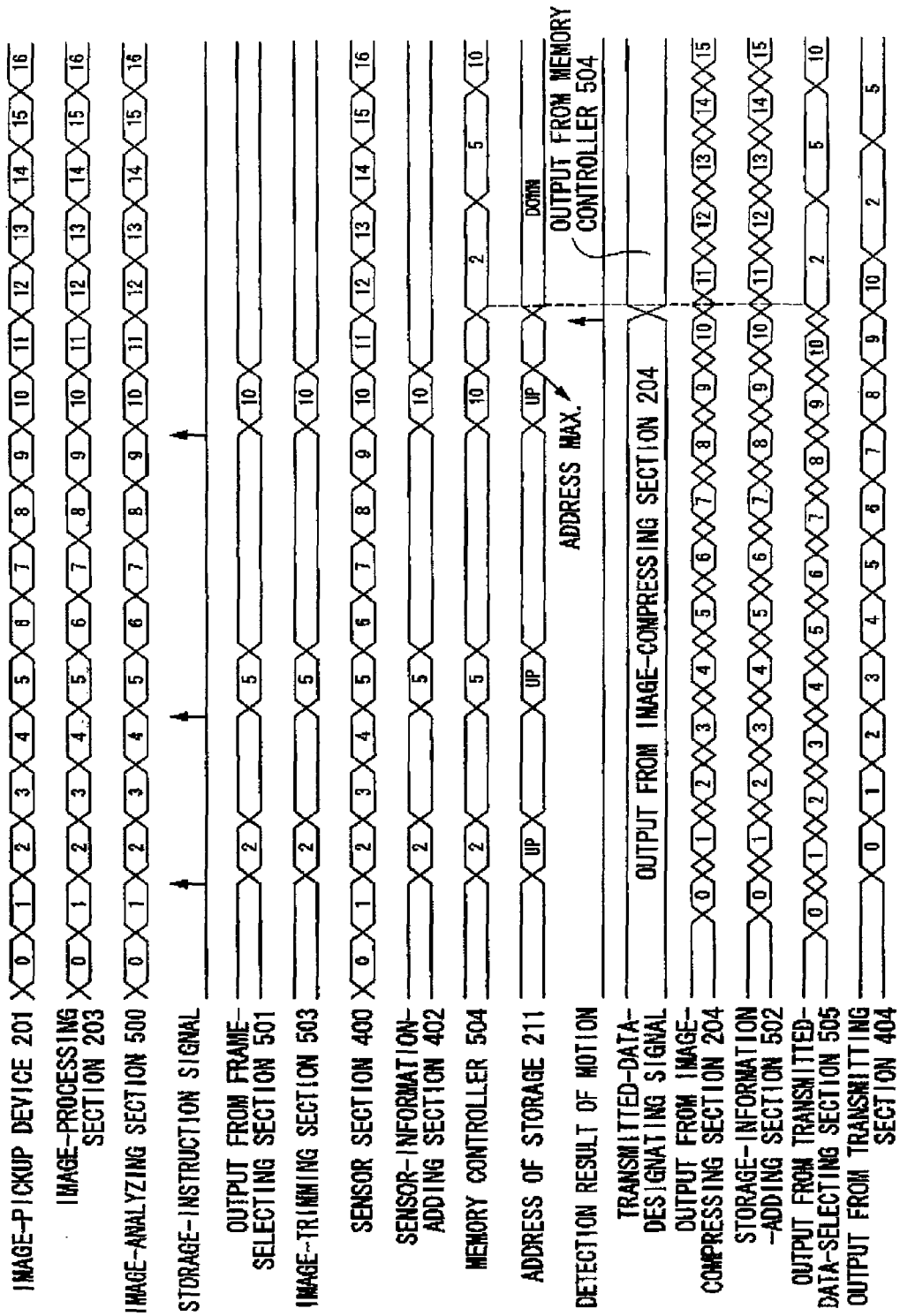
FIG. 25 is a timing diagram showing the operation conducted by the image-pickup apparatus according to the third embodiment of the present invention.

A timing diagram shown in FIG. 25 explains when the elements in the image-pickup apparatus 450 will be operated. The image-analyzing section 500 calculates a motion vector based on the image data output from the image-pickup device 201 and determines whether or not the image-pickup apparatus 450 is guided. The frame-selecting section 501 selects the frame subject to be stored in the storage 211 based on the determination result obtained by the image-analyzing section 500.

The storage-information-adding section 502 adds the information indicative of the frame stored in the storage 211 onto the encoded data that is output from the image-compressing section 204 and corresponds to the image data selected by the frame-selecting section 501. The image-trimming section 503 trims the image data corresponding to the central portion of tine image data selected by the frame-selecting section 501. The transmitted-data-selecting section 505 switches the encoded data output from the image-compressing section 204 and the image data stored in the storage 211 and outputs the selected data to the transmitting section 404 based on the information indicative of the remaining capacity of the storage 211 and on the information indicative of the motion of the image detected by using the image data output from the image-pickup device 201.

In the above-described image-pickup apparatus 450 according to the present embodiment, the image-analyzing section 500 analyzes the image data by detecting the motion between frames, and the frame-selecting section 501 selects the image data subject to be stored in the storage 211 based on the result of analysis. This configuration permits the image-pickup apparatus 450 to automatically select the image data subject to be stored in the storage 211 without receiving such a request from the exterior apparatus.

The image-analyzing section 500 according to the present embodiment maintains the information indicative of the image data preceding the frame subject to determination as to whether or not it is stored in the storage 211 and generates the information indicative of the difference between the frames based on the maintained information and the information indicative of the image data corresponding to the frame subject to the determination. This configuration allows selecting of the image data subject to be stored in the storage 211 based on the inter-frame changing state of image data. Thus, the image data subject to be stored in the storage 211 can be selected based on whether or not the image-pickup apparatus 450 is guided.

In particular, the changing state of image data can be detected by detecting the motion of the image according to the present embodiment. Furthermore, high quality image data corresponding to the non-guided state of the image-pickup apparatus 450 can be stored in the storage 211 by means of the frame-selecting section 501 for selecting the frame of image data subject to determination as to whether or not the image data should be stored in the storage 211 in a case where the value indicative of an inter-frame difference is equal to or less than the predetermined threshold.

Also, the selected-information-maintaining section 604 of the image-analyzing section 500 in the present embodiment maintains the information indicative of whether or not a frame of image data preceding the frame subject to determination as to whether or not the image data should be stored in the storage 211 is selected. In addition, if the preceding frame of image data is selected and the changing state of the image in the frame subject to determination is deemed not so significant, the frame-selecting section 501 does not select the image data subject to determination and to storage into the storage 211. This configuration allows the storage 211 to save the capacity because similar images do not have to be stored in the storage 211.

Furthermore, the image-trimming section 503 trims the image data corresponding to the central portion of the image data selected by the frame-selecting section 501 and the trimmed image data is stored in the storage 211 in the preset embodiment. Therefore, the capacity of the storage 211 can be saved significantly while maintaining the necessary image data.

The frame-selected section 501 according to the present embodiment also determines whether the frame of image data subject to determination should be stored in the storage 211 based on the result of analysis conducted by the image-analyzing section 500 with respect to the frame of image data preceding the frame subject to determination as to whether or not the image data is stored in the store 211. This configuration may allow omission of the buffers that have been, until obtaining the fixed determination, indispensable for maintaining the frame of image data subject to the determination as to whether the image data should be stored in the storage.

The storage-information-adding section 502 according to the present embodiment also adds the information indicative of whether or not the image data subject to storage in the storage 211 is selected onto the image data. This configuration can notify the exterior apparatus as to whether or not the image data is stored in the storage 211. Therefore, the doctor 300 guiding the image-pickup apparatus 450 while observing the image displayed on the monitor of the exterior apparatus 302 as shown in FIG. 7 cannot recognize whether or not high quality image data suitable for a still image of a portion subject to diagnosis can be obtained. Possibly, the operation has been conduced in vain if the obtained data reveals the lack of a necessary portion subject to diagnosis. However, the doctor 300 can guide the image-pickup apparatus 450 according to the present embodiment to a portion subject to diagnosis after recognizing that high quality image data is suitable for a still image of the portion subject to diagnosis.

The transmitted-data-selecting section 505 according to the present embodiment in view of the result of analyzing the image data and the remaining capacity of the storage 211 selects one of the image data (encoded data) output from the image-compressing section 204 and the image data (encoded data) stored in the storage 211 and outputs the selected image data to the transmitting section 404. This configuration permits the image-pickup apparatus 450 to automatically transmit high quality image data suitable for a still image for viewing use to the exterior apparatus without receiving such a request.

According to the present embodiment applied to an endoscope system, the image-pickup apparatus 450 using a guided capsule is advantageous in that the doctor 300 shown in FIG. 7 can guide the capsule endoscope 301 while observing the dynamic image displayed on the monitor of the exterior apparatus 302 and can obtain a high quality image based on the movement of the capsule endoscope 301.

Figure 26:
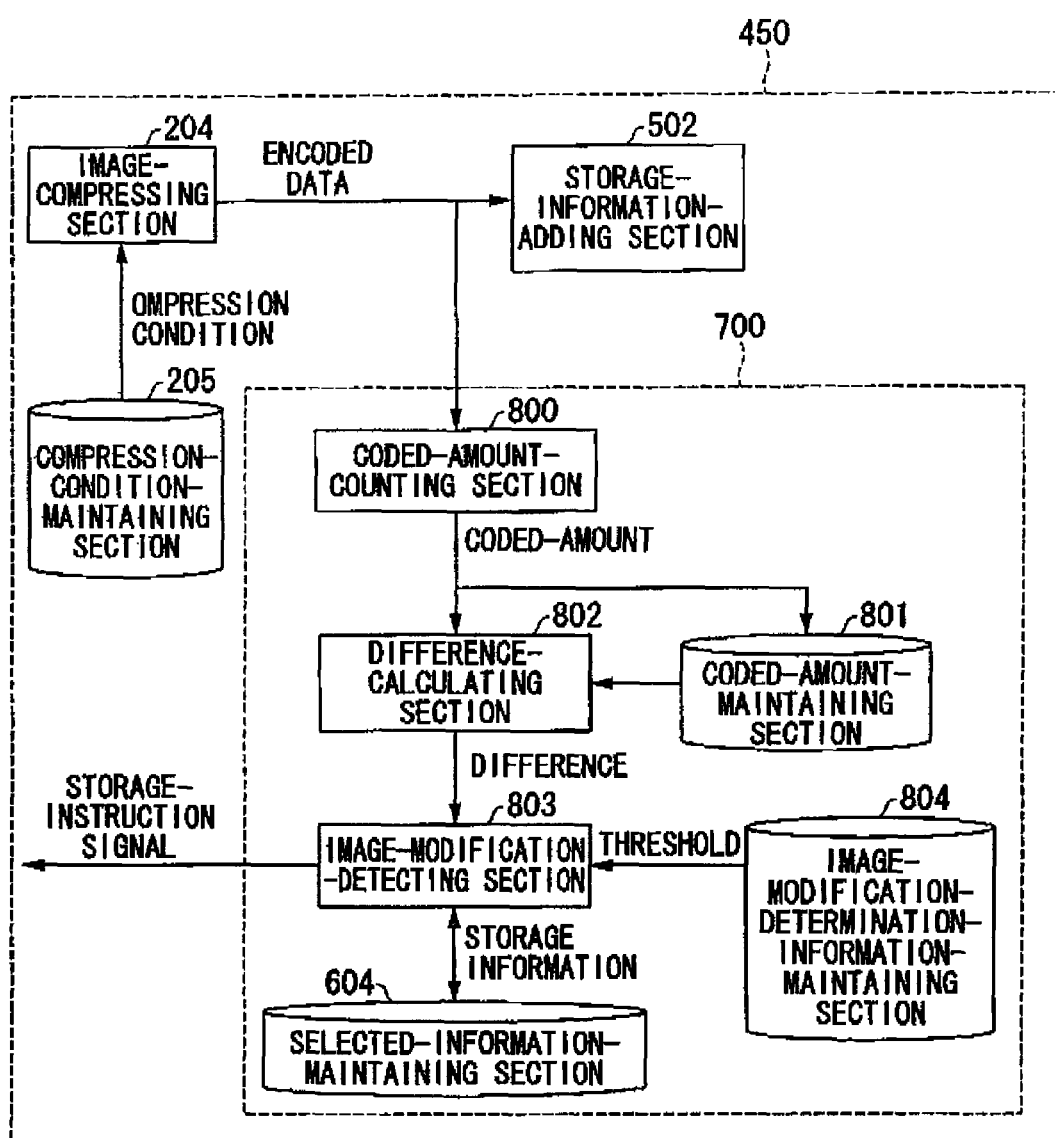
FIG. 26 is a block diagram showing another configuration of the image-pickup apparatus according to the third embodiment of the present invention.
Figure 27:
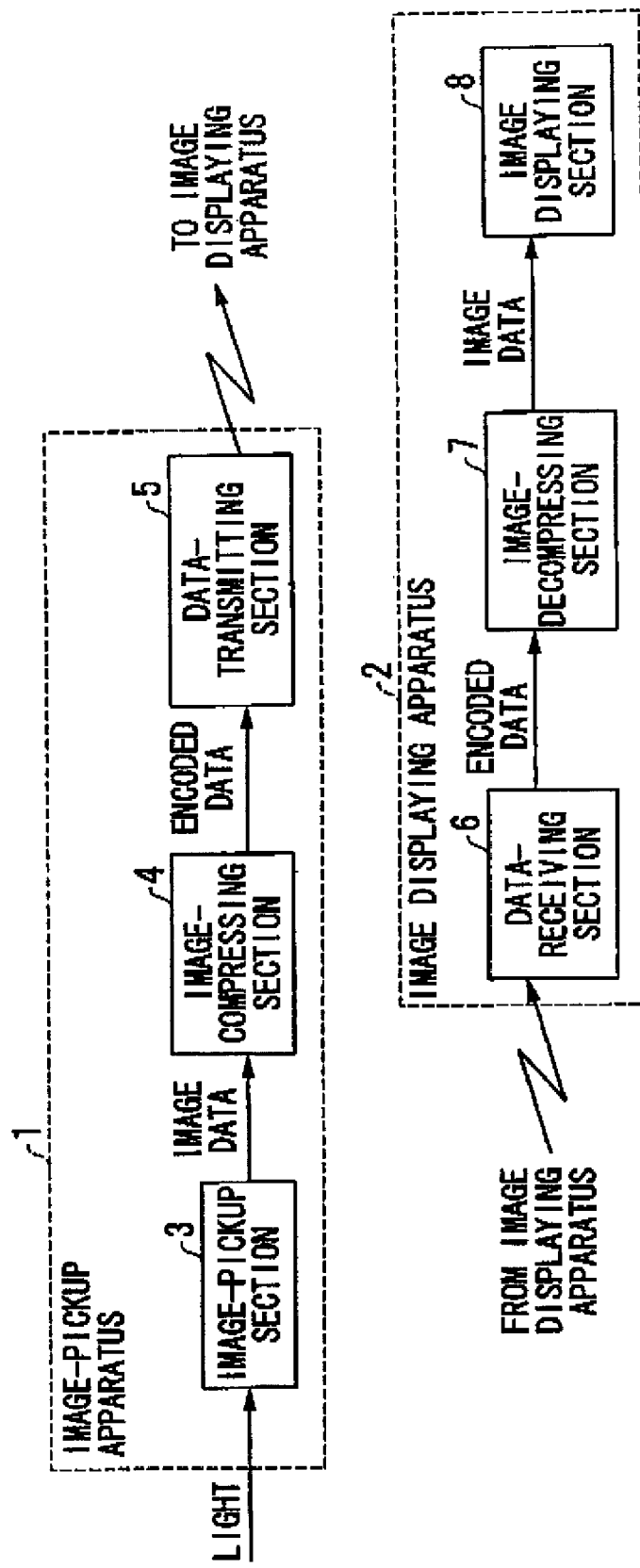
FIG. 27 is a schematic diagram of a conventional image-pickup-and-display system.
Figure 28:
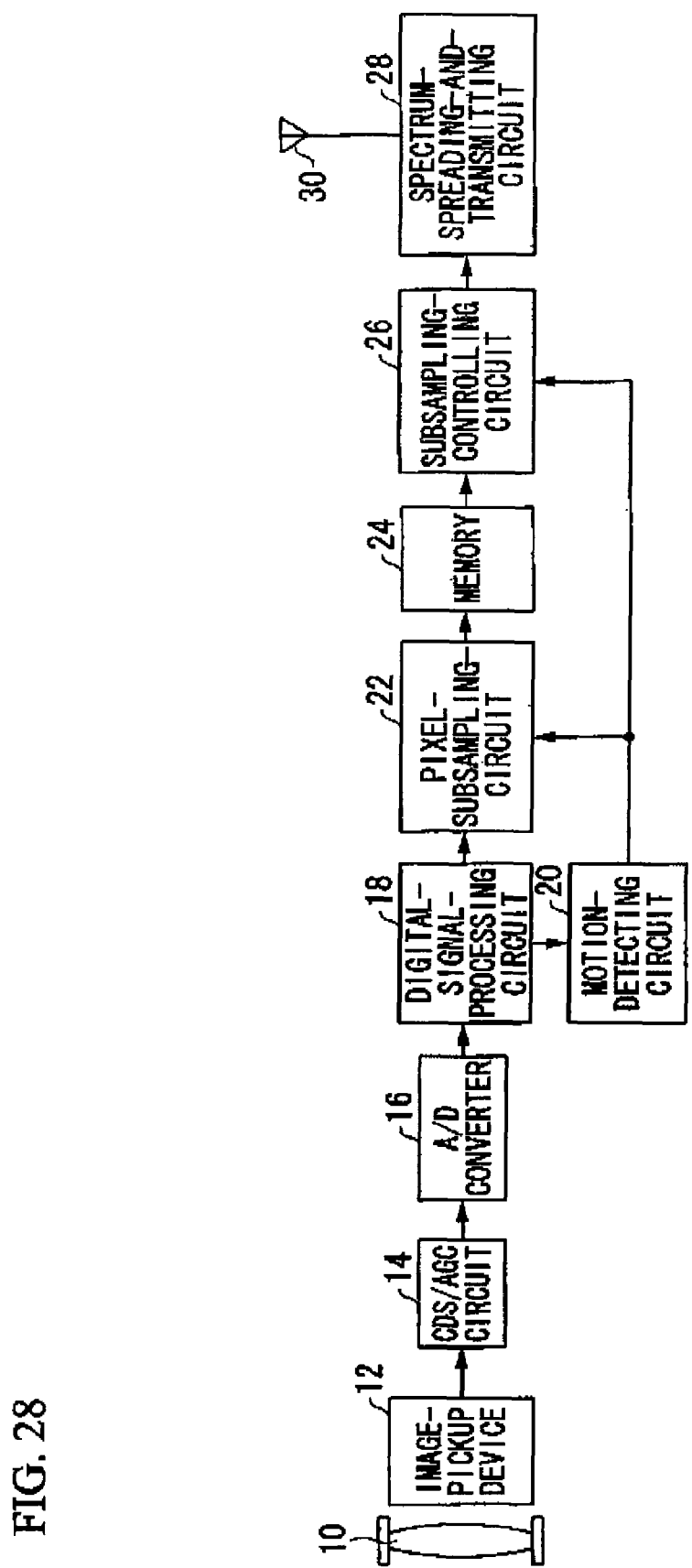
FIG. 28 is a block diagram of the conventional image-pickup-and-display system.

A modified embodiment of the image-analyzing section according to the present embodiment will be explained next. FIG. 26 illustrates another configuration of the image-pickup apparatus 450. The same reference numerals are added to the elements having the same functions as those illustrated in FIG. 14 so as to omit explanation of duplicated features; thus, only different features will be explained hereafter. The image-pickup apparatus 450 illustrated in FIG. 26 is characterized by a coded-amount-counting section 800, a coded-amount-maintaining section 801, a difference-calculating section 802, an image-modification-detecting section 803, and an image-modification-determination-information-maintaining section 804 that are provided to the image-analyzing section 700.

The image-analyzing section 700 using the coded amount of encoded data determines whether or not the image-pickup apparatus 450 is guided and generates a storage-instruction signal for selecting the frame subject to storage in the storage 211. The code-amount-counting section 800 counts the data amount of encoded data output from the image-compressing section 204 on a frame-basis and outputs its coded amount of incremental value. The coded-amount-maintaining section 801 maintains one frame of coded amount output from the coded-amount-counting section 800.

The difference-calculating section 802 outputs the difference in value between the coded amount of the preceding frame of encoded data maintained by the coded-amount-maintaining section 801 and the coded amount of the frame of encoded data which is subject to determination and is output from the coded-amount-counting section 800. The image-modification-detecting section 803 compares the difference in value output from the difference-calculating section 802 with the threshold maintained by the image-modification-determination-information-maintaining section 804 and generates a storage-instruction signal for selecting the frame subject to storage 211.

In a case where a quantization table stored in the compression-condition-maintaining section 205 shown in FIG. 26 is fixed, the coded amount of encoded data on a frame-basis output from the image-compressing section 204 depends on the image data input into the image-compressing section 204. Since the preceding frame of image data obtained by the image-pickup device 201 is substantially identical to the frame of image data subject to determination in a case where the image-pickup apparatus 450 is in a stationary state, the coded amount will also be substantially identical. Therefore, whether or not the image-pickup apparatus 450 is guided can be determined by analyzing the difference in value between the coded amount of the preceding frame of image data and the coded amount of the frame of image data subject to determination.

The image-modification-detecting section 803 having determined that the image-pickup apparatus 450 is in the stationary state outputs the storage-instruction signal indicative of storing the corresponding frame of image data in the storage 211. That is, the image-modification-detecting section 803 outputs the storage-instruction signal indicative of storing the image data subject to determination in the storage 211 in a case where the difference in value of the coded amount output from the difference-calculating section 802 is less than the threshold maintained by the image-modification-determination-information-maintaining section 804.

As explained above, the image-analyzing section 700 detects the changing state of an image based on the difference in value between the frames with respect to the coded amount of encoded data output from the image-compressing section 204 and determines whether or not the image-pickup apparatus 450 is guided by detecting whether or not the state of image is changing. This configuration including a counter-circuit for counting the coded amount, a difference circuit for calculating the difference value, and a memory for maintaining only the coded amount provide a determination as to whether or not the image-pickup apparatus 450 is guided. This configuration permits a simpler structure of the image-pickup apparatus 450 than that of the image-analyzing section 500 shown in FIG. 15 guiding the image-pickup apparatus 450 by using the motion vector.

Similarly to the first embodiment, the method for outputting the image data from the storage 211 to the storage 211 is not limited to the above methods in the present embodiment. For instance, the exterior apparatus may be adapted to obtain the image data from the storage 211 after the image-pickup apparatus 450 is removed from a patient's body.

The embodiment of the present invention have been explained above in detail with reference to the drawings. However, it should be understood that the drawings and detailed description thereof are not intended to limit the invention to the particular form disclosed; thus, the invention disclosed herein is susceptible to various modifications and alternative forms, i.e., design changes. For example, the operation associated with generating dynamic image data. e.g., picked up image, compressed and encoded image, and image subject to transmission may be stopped while the image data stored in the storage is transmitted to the exterior apparatus, and so may be at least a part of the operation for selecting the image data by means of the frame-selecting section. This configuration can reduce the power consumption of the image-pickup apparatus. The method is not limited to the above configuration since various application programs and the usage thereof may be used with respect to the optimal conditions for automatically generating signals including the storage-instruction signal, the pagination-designating signal, the compression-condition-designating signal, and the transmitted-data-designating signal by means of the image-pickup apparatus.

Since the image data obtained by the image-pickup device is transmitted to the exterior apparatus by the transmitting unit at the same time when the image data obtained by the image-pickup device is stored in the storage unit, the present invention is advantageous because both image data having a high frame rate suitable for a dynamic image and high quality image data suitable for a still image can be obtained.

What is claimed is:

1. A capsule endoscope comprising:
   an image pickup section configured to sequentially provide a color image data of an image pickup region;
   an analyzing section configured to analyze the color image data from the image pickup section, select one of a plurality of image processions which are predetermined based on the analysis result, and perform image processing;
   a transmitting section configured to transfer the color image data outside of a human body; and
   a magnet for operating the capsule endoscope by externally applying a magnetic force;
   a motion-detecting section provided in the analyzing section;
   a motion-determination section provided in the motion-detecting section; and
   an image-data-storage section provided in the analyzing section, wherein the analyzing section detects a movement of the image pickup region from successive color images the image-data-storage section stores the image data when the motion-determination section determines that the capsule endoscope is in "motionless" and a frame of the image data is not stored, the motion-determination section determines that the capsule endoscope is in "motion" when the result value of the motion-determining is greater than a threshold value, and the capsule endoscope is in "motionless" when the result value of the motion-determining is smaller than the threshold value, when a write address of the image-data-storage section reaches a maximum and the motion-determination section determines the capsule endoscope is in "motion", the motion-determination section gives priority to outputting information from the image pickup section to outside of a human body, and when a write address of the image-data-storage section reaches a maximum and the motion-determination section determines the capsule endoscope is in "motionless", the motion-determination section gives priority to outputting information of the image-data-storage section to outside of the human body.

2. The capsule endoscope according to the claim 1, further comprising:

an image data compressing section, wherein the transmitting section transmits a compressed color image data by the image data compressing section outside of a human body.

3. The capsule endoscope according to the claim 1, wherein the plurality of image processions include a procession of storing a compressed color image which is compressed at lower than a specified data compression rate in the image data storage section.

4. The capsule endoscope according to claim 1, wherein the motion-determination section determines the result value according to a difference value of a motion vector extracted from within continuous images.

5. The capsule endoscope according to claim 1, further comprising:

an image-compressing section provided in the analyzing section, wherein the motion-determination section determines the result value according to a difference value of a coded-amount of compressed continuous images.

6. The capsule endoscope according to claim 1, wherein:

the motion-determination section adds information indicative of whether the frame of the image data is stored in the image-data-storage section to the image data from the image-pickup section and the motion-determination section outputs the information to outside of a human body.

* * * * *